(12) United States Patent
Van Dam et al.

(10) Patent No.: US 7,829,032 B2
(45) Date of Patent: Nov. 9, 2010

(54) FULLY-AUTOMATED MICROFLUIDIC SYSTEM FOR THE SYNTHESIS OF RADIOLABELED BIOMARKERS FOR POSITRON EMISSION TOMOGRAPHY

(75) Inventors: Robert Michael Van Dam, Glendale, CA (US); Carroll Edward Ball, San Diego, CA (US); Arkadij M. Elizarov, Valley Village, CA (US); Hartmuth C. Kolb, Playa Del Rey, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 335 days.

(21) Appl. No.: 12/011,220

(22) Filed: Jan. 23, 2008

(65) Prior Publication Data

US 2008/0233018 A1    Sep. 25, 2008

Related U.S. Application Data

(60) Provisional application No. 60/897,002, filed on Jan. 23, 2007.

(51) Int. Cl.
*B01J 19/00* (2006.01)
(52) U.S. Cl. ..................................... 422/159
(58) Field of Classification Search .............. 422/99, 422/100, 159
See application file for complete search history.

(56) References Cited

U.S. PATENT DOCUMENTS

| | | | |
|---|---|---|---|
| 2,716,017 A | 8/1955 | Linker | |
| 3,613,729 A | 10/1971 | Dora | |
| 4,536,121 A | 8/1985 | Stewart et al. | |
| 4,696,195 A | 9/1987 | Savonlahti et al. | |
| 4,721,133 A | 1/1988 | Sundblom | |
| 4,924,241 A | 5/1990 | Parks et al. | |
| 4,977,948 A | 12/1990 | Chandley | |
| 5,413,227 A | 5/1995 | Diebold et al. | |
| 5,624,556 A | 4/1997 | Kutowy et al. | |
| 5,679,580 A | 10/1997 | Ball et al. | |
| 5,765,591 A | 6/1998 | Wasson et al. | |

(Continued)

FOREIGN PATENT DOCUMENTS

WO    WO 9322058    11/1993

(Continued)

OTHER PUBLICATIONS

Dharmatilleke, S., et al. "Three-dimensional silicone microfluidic interconnection scheme using sacrificial wax filaments", Proceedings of SPIE, vol. 4177, pp. 83-90, Aug. 28, 2006.

(Continued)

*Primary Examiner*—Walter D Griffin
*Assistant Examiner*—Christopher K VanDeusen
(74) *Attorney, Agent, or Firm*—Joshua Ryan

(57) ABSTRACT

The present application relates to microfluidic devices and related technologies, and to chemical processes using such devices. More specifically, the application discloses a fully automated synthesis of radioactive compounds for imaging, such as by positron emission tomography (PET), in a fast, efficient and compact manner. In particular, this application describe an automated, stand-alone, microfluidic instrument for the multi-step chemical synthesis of radiopharmaceuticals, such as probes for PET and a method of using such instruments.

45 Claims, 21 Drawing Sheets

U.S. PATENT DOCUMENTS

| | | | |
|---|---|---|---|
| 5,863,502 | A | 1/1999 | Southgate et al. |
| 5,988,603 | A | 11/1999 | McCampbell et al. |
| 5,989,402 | A | 11/1999 | Chow et al. |
| 6,065,195 | A | 5/2000 | Chatterjee et al. |
| 6,145,810 | A | 11/2000 | Connolly et al. |
| 6,399,025 | B1 | 6/2002 | Chow |
| 6,416,642 | B1* | 7/2002 | Alajoki et al. ............... 204/451 |
| 6,431,976 | B1 | 8/2002 | Auquier |
| 6,720,710 | B1 | 4/2004 | Wenzel et al. |
| 6,752,371 | B2 | 6/2004 | Herbert et al. |
| 6,814,337 | B2 | 11/2004 | Schmaltz |
| 6,830,545 | B2* | 12/2004 | Bendall ....................... 600/114 |
| 6,830,729 | B1 | 12/2004 | Holl et al. |
| 6,929,030 | B2 | 8/2005 | Unger et al. |
| 7,040,338 | B2 | 5/2006 | Unger et al. |
| 7,144,568 | B2 | 12/2006 | Ricard et al. |
| 7,223,363 | B2 | 5/2007 | McNeely et al. |
| 2001/0012612 | A1 | 8/2001 | Petersen |
| 2002/0010381 | A1* | 1/2002 | Soundararajan ............... 588/19 |
| 2002/0048536 | A1 | 4/2002 | Bergh et al. |
| 2002/1666585 | | 11/2002 | O'Connor et al. |
| 2003/0008308 | A1 | 1/2003 | Enzelberger et al. |
| 2003/0019833 | A1 | 1/2003 | Unger et al. |
| 2003/0175947 | A1 | 9/2003 | Liu et al. |
| 2003/0214057 | A1 | 11/2003 | Huang |
| 2004/0022696 | A1* | 2/2004 | Zigler et al. ................ 422/159 |
| 2004/0037739 | A1 | 2/2004 | McNeely et al. |
| 2004/0101444 | A1 | 5/2004 | Sommers et al. |
| 2004/0242953 | A1* | 12/2004 | Good ............................ 600/7 |
| 2005/0265906 | A1* | 12/2005 | Najafi ......................... 422/159 |
| 2006/0078475 | A1 | 4/2006 | Tai et al. |
| 2006/0150385 | A1 | 7/2006 | Gilligan et al. |
| 2006/0163069 | A1 | 7/2006 | Prak et al. |
| 2007/0012891 | A1 | 1/2007 | Maltezos |
| 2007/0051412 | A1* | 3/2007 | Heath et al. ............. 137/561 R |
| 2007/0272309 | A1 | 11/2007 | Rehm et al. |
| 2008/0224072 | A1* | 9/2008 | Sonnenhol et al. ....... 250/496.1 |

FOREIGN PATENT DOCUMENTS

| | | |
|---|---|---|
| WO | WO 9511080 | 4/1995 |
| WO | WO 00/43766 | 7/2000 |
| WO | 0073412 | 12/2000 |
| WO | 0141931 | 6/2001 |
| WO | 0173417 | 10/2001 |
| WO | 0240874 | 5/2002 |
| WO | 02070932 | 9/2002 |
| WO | 02072264 | 9/2002 |
| WO | 03024597 | 3/2003 |
| WO | WO 03087410 A1 * | 10/2003 |
| WO | WO 03098219 | 11/2003 |
| WO | 2006060748 | 6/2006 |
| WO | WO 2006/071470 | 7/2006 |
| WO | WO 03/078358 | 9/2006 |
| WO | WO 2006/098817 | 9/2006 |
| WO | WO 2006/116629 | 11/2006 |
| WO | WO 2007/027928 | 3/2007 |
| WO | WO 2007/041486 | 4/2007 |
| WO | WO 2007/092472 | 8/2007 |

OTHER PUBLICATIONS

Unger, M.A., et al., "Monolithic Microfabricated Valves and Pumps by Multilayer Soft Lithography", Science, vol. 288, No. 5463, pp. 113-116 (Apr. 2000).

Thorsen, T., et al., "Microfluidic Large-Scale Integration", Science, vol. 298, No. 5593, pp. 580-584 (Sep. 2002).

Rolland, J.P., et al., "Solvent-Resistant Photocurable 'Liquid Teflon' for Microfluidic Device Fabrication", JACS, vol. 126, pp. 2322-2323 (2004).

Van Dam, R.M., "Solvent-Resistant Elastomeric Microfluidic Devices and Applications", PhD Thesis, California Institute of Technology (Aug. 2005).

Studer, V., et al., "Scaling Properties of a Low-Actuation Pressure Microfluidc Valve", Journal of Applied Physics, 95 (1), pp. 393-398 (2004).

Fredrickson, C.K., et al., "Macro-to-Macro Interfaces for Microfluidic Devices", Lab on a Chip, 4, pp. 526-533 (20004).

Gu, W., "Computerized Microfluidic Cell Culture Using Elastomeric Channels and Braille Displays", PNAS, vol. 101, No. 45, pp. 15861-15866 (2004).

Lai, S. M., et al. "Knoevenagel condensation reaction in a membrane microreactor" Chem. Commun, 2003, 218-219.

Yamamoto, T. et al., "PDMS-glass hybrid microreactor array with embedded temperature control device. Application to cell-free protein synthesis", Lab Chip, 2002, 2, 197-202.

Psaltis, D. et al. "Developing optofluidic technology through the fusion of microfluidics and optics", Nature, 2005, 442, 381-386.

Grover, W., H. et al., "Monolithic membrane valves and diaphragm pumps for practical large-scale integration into glass microfluidic devices" Sensors and Actuators E, 2003, 89, 315-323.

Lee, C. C. et al., "Miltistep Synthesis of a Radiolabeled Imaging Probe Using Integrated Microfluics", Science, 2005, 310, 1793-1979.

Gillies, J. M. et al., "Microfluidic reactor for the radiosynthesis of PET radiotracers", J. Appl. Rad. Isot. 2005, 64, 325-332.

Yuen, P.K. et al., "Semi-disposable microvalves for use iwth microfabricated devices or microchips", J. Micromech. Microeng. 2000, 10, 401-409.

* cited by examiner

FIG. 2B

FLUID LAYER

VENT LAYER

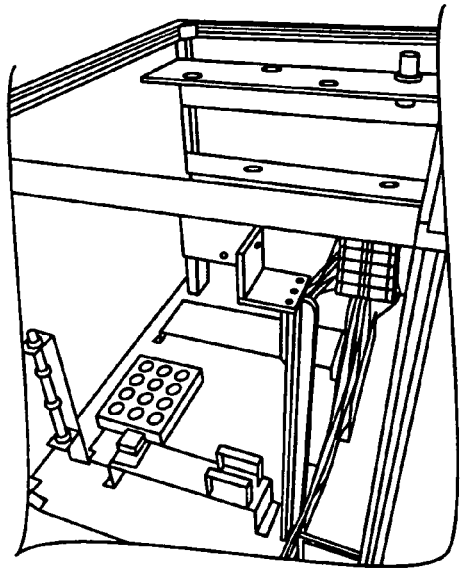 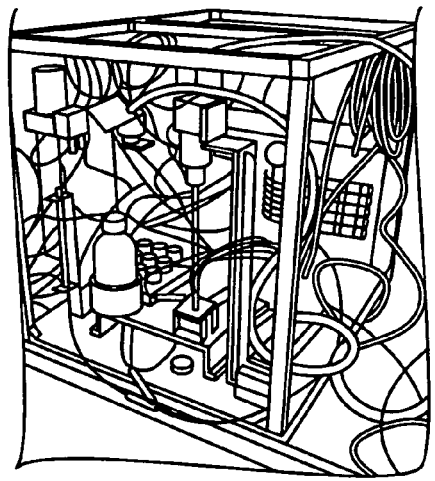
FIG. 10A  FIG. 10B
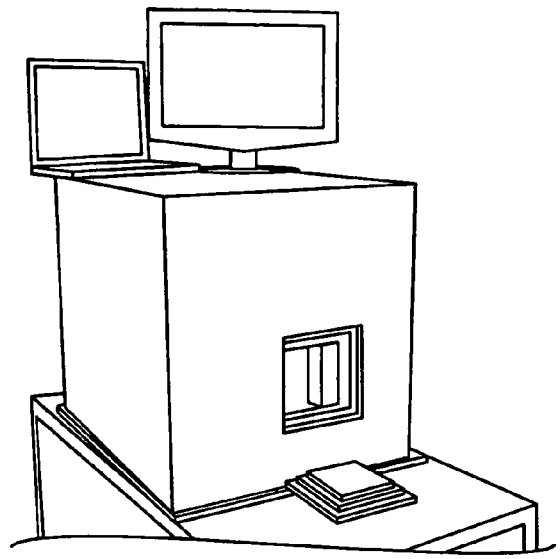
FIG. 10C

TABLE OF ASSIGNMENTS OF ANALOG I/O (INPUT/OUTPUT)

| ANALOG INPUT ASSIGNMENTS | | | |
|---|---|---|---|
| MICHAEL VAN DAM | | | |
| 2006 11 17 | | | |
| | | | |
| | | DATABASE NAME | DESCRIPTION |
| | | | |
| AI | 01 | REACTOR_TEMP | MEASURED TEMPERATURE OF REACTOR |
| AI | 02 | TRAP_VOLTAGE | FEEDTHROUGH OF HIGH VOLTAGE SETPOINT |
| AI | 03 | VENT_PRESSURE | PRESSURE IN VENT CHANNEL OF REACTOR CHIP |
| AI | 04 | RAD_F18H2O_VIAL | RADIOACTIVITY IN F18H2O VIAL FROM CYCLOTRON |
| AI | 05 | RAD_TRAP | RADIOACTIVITY IN TRAP |
| AI | 06 | RAD_REACTOR_CHIP | RADIOACTIVITY IN REACTOR CHIP |
| AI | 07 | RAD_RAW_PRODUCT_VIAL | RAIDOACTIVITY IN RAW PRODUCT VIAL |
| AI | 08 | RAD_PRODUCT_VIAL | RADIOACTIVITY IN FINAL PRODUCT VIAL |
| AI | 09 | RAD_VACUUM_TRAP | RADIOACTIVITY IN VACUUM TRAP |
| AI | 10 | | |
| AI | 11 | | |
| AI | 12 | | |
| AI | 13 | | |
| AI | 14 | RAD_CHANNEL_1 | RADIOACTIVITY, CHANNEL 1 |
| AI | 15 | RAD_CHANNEL_2 | RADIOACTIVITY, CHANNEL 2 |
| AI | 16 | RAD_CHANNEL_3 | RADIOACTIVITY, CHANNEL 3 |
| | | | |

| ANALOG OUTPUT ASSIGNMENTS | | | |
|---|---|---|---|
| MICHAEL VAN DAM | | | |
| 2006 09 27 | | | |
| | | | |
| | | DATABASE NAME | DESCRIPTION |
| AO | 01 | REACTOR_TEMP_SETPOINT | TEMPERATURE CONTROLLER TEMPERAT |
| AO | 02 | TRAP_VOLTAGE_SETPOINT | HIGH VOLTAGE SUPPLY VOLTAGE-SETP |
| AO | 03 | | |
| AO | 04 | | |
| AO | 05 | | |
| AO | 06 | | |
| AO | 07 | | |
| AO | 08 | | |
| AO | 09 | | |
| AO | 10 | | |

FIG. 11A

FIG. 11B MAP

TABLE OF ASSIGNMENTS OF DIGITAL I/O (INPUT/OUTPUT)

DIGITAL OUTPUT ASSIGNMENTS
MICHAEL VAN DAM
2006 11 23

| | I/O PIN | DATABASE NAME | DESCRIPTION | 0-STATE NAME |
|---|---|---|---|---|
| DO | 01 | CHIP_VALVE_TRAP_F18N | | CLOSED |
| DO | 02 | CHIP_VALVE_TRAP_ELUENT | | CLOSED |
| DO | 03 | CHIP_VALVE_TRAP_WASTE | | CLOSED |
| DO | 04 | CHIP_VALVE_TRAP_F18OUT | | CLOSED |
| DO | 05 | CHIP_VALVE_REACTOR_F18 | | CLOSED |
| DO | 06 | CHIP_VALVE_REACTOR_MT | | CLOSED |
| DO | 07 | CHIP_VALVE_REACTOR_HCL | | CLOSED |
| DO | 08 | CHIP_VALVE_REACTOR_EXTRA | | CLOSED |
| DO | 09 | CHIP_VALVE_REACTOR_H2O | | CLOSED |
| DO | 10 | CHIP_VALVE_REACTOR_PRODUCT | | CLOSED |
| DO | 11 | TRAP_VOLTAGE_ENABLE | ENABLE HIGH VOLTAGE POWER SUPPLY | OFF |
| DO | 12 | TRAP_VOLTAGE_POLARITY | POLARITY OF HIGH VOLTAGE SUPPLY | POS |
| DO | 13 | REACTOR_COOLER_ENABLE | ENABLE/POWER REACTOR COOLER | OFF |
| DO | 14 | VALVE_COLUMN_SELECT | SELECT POSITION OR ROTARY VALVE (1-ELUTE, 2-TRAP) | ELUTE |
| DO | 15 | CHIP_LIGHT_ENABLE | ENABLE ILLUMINATION FOR CHIP CAMERA | OFF |
| DO | 16 | VACUUM_PUMP_ENABLE | ENABLE VACUUM PUMP | OFF |

FIG. 11B-1

| 1-STATE NAME | DEFAULT POWER-ON STATE | 0-STATE DESCRIPTION | 1-STATE DESCRIPTION |
|---|---|---|---|
| OPEN | CLOSED | | ADMIT F18 INTO TRAP CHIP |
| OPEN | CLOSED | | ADMIT K222/K2O03-REAGENT INTO TRAP CHIP |
| OPEN | CLOSED | | ALLOW WASTE TO EXIT FROM TRAP CHIP |
| OPEN | CLOSED | | ALLOW F18 TO EXIT TRAP CHIP |
| OPEN | CLOSED | | ADMIT F18 INTO REACTOR CHIP |
| OPEN | CLOSED | | ADMIT MT-REAGENT INTO REACTOR CHIP |
| OPEN | CLOSED | | ADMIT HCL-REAGENT INTO REACTOR CHIP |
| OPEN | CLOSED | | ADMIT EXTRA-REAGENT INTO REACTOR CHIP |
| OPEN | CLOSED | | ADMIT H2O-REAGENT INTO REACTOR CHIP |
| OPEN | CLOSED | | ALLOW PRODUCT TO EXIT REACTOR CHIP |
| ON | OFF | | |
| NEG | POS | | |
| ON | OFF | REACTOR COOLER IS DISABLED | REACTOR COOLER IS ENABLED |
| TRAP | TRAP | | |
| ON | OFF | | |
| ON | OFF | | |

FIG. 11B-2

| | | | |
|---|---|---|---|
| DO | 17 | VALVE_VENT_VACUUM | OFF |
| DO | 18 | VALVE_VENT_PRESSURIZE | OFF |
| DO | 19 | VALVE_CHIP_H2O_SELECT | H2OLINE |
| DO | 20 | VALVE_MECN_LINE_SELECT | MECN |
| DO | 21 | VALVE_MECN_PRESSURIZE | VENT |
| DO | 22 | VALVE_TRAP_ELUENT_LINE_SELECT | ELUENT |
| DO | 23 | VALVE_TRAP_ELUENT_PRESSURIZE | VENT |
| DO | 24 | VALVE_F18H2O_LINE_SELECT | F18H2O |
| DO | 25 | VALVE_F18H2O_PRESSURIZE | VENT |
| DO | 26 | VALVE_MT_LINE_SELECT | MT |
| DO | 27 | VALVE_MT_PRESSURIZE | VENT |
| DO | 28 | VALVE_HCL_LINE_SELECT | HCL |
| DO | 29 | VALVE_HCL_PRESSURIZE | VENT |
| DO | 30 | VALVE_EXTRA_LINE_SELECT | EXTRA |
| DO | 31 | VALVE_EXTRA_PRESSURIZE | VENT |
| DO | 32 | VALVE_H2O_LINE_SELECT | H2O |
| DO | 33 | VALVE_H2O_PRESSURIZE | VENT |
| DO | 34 | VALVE_TRAP_WASTE_SELECT | GENERAL |
| DO | 35 | VALVE_DEAD_VOLUME_BYPASS | CLOSED |
| DO | 36 | VALVE_RAW_PRODUCT_PRESSURIZE | VENT |

FIG. 11B-3

| ON | OFF | | CORRECT CHIP VENT CHANNEL TO VACUUM |
|---|---|---|---|
| ON | OFF | | CORRECT CHIP VENT CHANNEL TO PRESSURE |
| WASTE | H2OLINE | | |
| N2 | MECN | SELECT MECN INTO WASH LINE | SELECT N2 INTO WASH LINE |
| PRES | VENT | VENT MECN REAGENT VIAL | PRESSURIZE MECN REAGENT VIAL |
| MECNLINE | ELUENT | SELECT K2003/K222-REAGENT INTO TRAP ELUENT | SELECT WASH INTO TRAP ELUENT LINE |
| PRES | VENT | VENT K2003/K222 REAGENT VIAL | PRESSURIZE K2003/K222 REAGENT VIAL |
| H2OLINE | F18H2O | SELECT F18H2O INTO F18H2O LINE | SELECT H2O WASH INTO F18H2O LINE |
| PRES | VENT | VENT F18H2O VIAL | PRESSURIZE F18H2O VIAL |
| MECNLINE | MT | SELECT MT INTO MT LINE | SELECT WASH INTO MT LINE |
| PRES | VENT | VENT MT VIAL | PRESSURIZE MT VIAL |
| H2OLINE | HCL | SELECT HCL INTO HCL LINE | SELECT H2O WASH INTO HCL LINE |
| PRES | VENT | VENT HCL VIAL | PRESSURIZE HCL VIAL |
| MECNLINE | EXTRA | | |
| PRES | VENT | | |
| N2 | H2O | SELECT H2O INTO H2O LINE | SELECT N2 INTO H2O LINE |
| PRES | VENT | VENT H2O VIAL | PRESSURIZE H2O VIAL |
| H2O18 | GENERAL | | DIVERT WASTE TO H2O18 CONTAINER |
| OPEN | CLOSED | | |
| PRES | VENT | | |

FIG. 11B-4

| | | | | | |
|---|---|---|---|---|---|
| DO | 37 | REACTOR_TEMP_CONTROL_ENABLE | ENABLE/POWER TEMPERATURE CONTROLLER (CONTROLS AC 1) | | OFF |
| DO | 38 | REACTOR_HEATER_ENABLE | ENABLE/POWER REACTOR HEATER (CONTROLS AC2) | | OFF |
| DO | 39 | - NOT AVAILABLE - | (CONTROLS AC 3) | | |
| DO | 40 | - NOT AVAILABLE - | (CONTROLS AC 4) | | |
| AC | 41 | (SEE DO37) | ** OUTPUT OF DO37 PROVIDED HERE, NOT WITH DIGITAL OUTS ** | | |
| AC | 42 | (SEE DO38) | ** OUTPUT OF DO38 PROVIDED HERE, NOT WITH DIGITAL OUTS ** | | |
| AC | 43 | (SEE DO39) | | | |
| AC | 44 | (SEE DO40) | | | |
| AC | 45 | - NOT CONTROLLED - | | | |
| AC | 46 | - NOT CONTROLLED - | | | |
| AC | 47 | - NOT CONTROLLED - | | | |
| AC | 48 | - NOT CONTROLLED - | | | |
| | | NOTE: PREVIOUS VALUE OF COLUMN SELECT VALVES (BEFORE ROTARY VALVE INSTALLATION): | | | |
| DO | 11 | VALVE_COLUMN_A_SELECT | | | WASTE |
| DO | 12 | VALVE_COLUMN_B_SELECT | | | F18IN |

FIG. 11B-5

FULLY-AUTOMATED MICROFLUIDIC SYSTEM FOR THE SYNTHESIS OF RADIOLABELED BIOMARKERS FOR POSITRON EMISSION TOMOGRAPHY

RELATED APPLICATION

This application claims priority to U.S. Provisional Application No. 60/897,002 filed Jan. 23, 2007, the contents of which is hereby incorporated in its entirety by reference.

FIELD OF THE INVENTION

The present application relates to microfluidic devices and related technologies, and to chemical processes using such devices. More specifically, the application discloses a fully automated synthesis of radioactive compounds for imaging, such as by positron emission tomography (PET), in a fast, efficient and compact manner. In particular, this application describes an automated, stand-alone, microfluidic instrument for the multi-step chemical synthesis of radiopharmaceuticals, such as probes for PET and methods of using such systems.

BACKGROUND OF THE INVENTION

Positron Emission Tomography is a molecular imaging technology that is increasingly used for detection of disease. PET imaging systems create images based on the distribution of positron-emitting isotopes in the tissue of a patient. The isotopes are typically administered to a patient by injection of probe molecules that comprise a positron-emitting isotope, e.g. carbon-11, nitrogen-13, oxygen-15, or fluorine 18, covalently attached to a molecule that is readily metabolized or localized in the body or that chemically binds to receptor sites within the body. For PET probes the short half-lives of the positron emitters require that synthesis, analysis and purification of the probes are completed rapidly.

Large-volume synthesis modules have been developed and used for the preparation of a number of radiopharmaceutical compounds. Common pharmaceuticals radiolabeled with F-18 include 2-deoxy-2-[F-18]-fluoro-D-glucose ($^{18}$F-FDG), 3'-deoxy-3'-[F-18]-fluorothymidine ($^{18}$F-FLT), 9-[4-[F-18] fluoro-3-(hydroxymethyl)butyl]guanine ($^{18}$F-FHBG), 9-[(3-[F-18] fluoro-1-hydroxy-2-propoxy)methyl]guanine ($^{18}$F-FHPG), 3-(2'-[F-18] fluoroethyl)spiperone ($^{18}$F-FESP), 4-[F-18] fluoro-N-[2-[1-(2-methoxyphenyl)-1-piperazinyl] ethyl]-N-2-pyridinyl-benzamide ($^{18}$F-p-MPPF), 2-(1-{6-[(2-[F-18]fluoroethyl)-(methyl)amino]-2-naphthyl}ethylidine) malononitrile ($^{18}$F-FDDNP), 2-[F-18] fluoro-α-methyltyrosine, [F-18] fluoromisonidazole ($^{18}$F-FMISO), 5-[F-18] fluoro-2'-deoxyuridine ($^{18}$F-FdUrd). Other common radiolabeled compounds include $^{11}$C-methionine and $^{11}$C-acetic acid. Large volume synthesis modules occupy a large amount of space and the chemical process requires longer reaction time cycles than desired for the preparation of the labeled compounds. Such modules are also difficult to modify for the research and development of new compounds and probes. Generally the reactions in such modules take place with reduced efficiency due to the tremendous dilution of reagents necessary for macroscopic liquid handling.

The synthesis of the [F-18]-labeled molecular probe, 2-deoxy-2-[F-18]-fluoro-D-glucose ($^{18}$F-FDG) is based on three major sequential synthetic processes: (i) Concentration of the dilute [F-18] fluoride solution (1-10 ppm) that is obtained from the bombardment of target water, [O-18]H$_2$O, in a cyclotron; (ii) [F-18]fluoride substitution of the mannose triflate precursor; and (iii) acidic hydrolysis of the fluorinated intermediate. Presently, [F-18]FDG is produced on a routine basis in a processing time (or cycle time) of about 50 minutes using macroscopic commercial synthesizers. These synthesizers consist, in part, of an HPLC pump, mechanical valves, glass-based reaction chambers and ion-exchange columns. The physical size of these units is approximately 80 cm×40 cm×60 cm. Descriptions of macroscopic synthesizers can be found in WO 2007/066089, WO 2005/057589, US 2007/0031492, and US 2004/022696.

Because of the long processing times and low reagent concentrations of macroscopic synthesizers and the short half-life of [F-18]fluorine ($t_{1/2}$=109.7 min), a considerable decrease in the radiochemical yields of the resulting probe are inevitably obtained. Moreover, because a number of commercialized automation system are constructed for macroscopic synthesis, the process requires the consumption of large amount of valuable reagents (e.g. mannose triflate or other such reagents), which is inefficient and wasteful for performing research at the smaller scale. For example, the required radioactivity for [F-18]FDG PET imaging of a single patient is about 20 mCi, which corresponds to about 240 ng of FDG. However, for small animal imaging applications, such as for a mouse, only about 200 μCi or less of [F-18]FDG is required.

Accordingly, there is a need to develop smaller or miniaturized systems and devices that are capable of processing such small quantities of molecular probes. In addition, there is a need for such systems that are capable of expediting chemical processing to reduce the overall processing or cycle times, simplifying the chemical processing procedures, and at the same time, provide the flexibility to produce a wide range of probes, biomarkers and labeled drugs or drug analogs, inexpensively.

Microfluidic devices can offer a variety of advantages over macroscopic reactors, such as reduced reagent consumption, high concentration of reagents, high surface-to-volume ratios, and improved control over mass and heat transfer. (See, K. Jahnisch, V. Hessel, H. Lowe, M. Baerns, *Angew. Chem.* 2004, 116: 410-451; *Angew. Chem. Int. Ed. Engl.* 2004, 43:406-446; P. Watts, S. J. Haswell, *Chem. Soc. Rev.* 2005, 34:235-246; and G. Jas, A. Kirschning, *Chem. Eur. J.* 2003, 9:5708-5723.)

SUMMARY OF THE INVENTION

The present application relates to microfluidic devices and related technologies, and to chemical processes using such devices. More specifically, the application discloses a fully automated synthesis of radioactive compounds for imaging, such as by positron emission tomography (PET), in a fast, efficient and compact manner. In particular, this application describes an automated, stand-alone, microfluidic instrument for the multi-step chemical synthesis of radiopharmaceuticals, such as probes for PET.

BRIEF DESCRIPTION OF THE FIGURES

FIG. 2A-B are screenshots from a representative automation program. (a) Graphical representation of system hardware to show temperature and pressure readout and allow manual control of individual valves and other components, or to allow initiation of series of steps via buttons in right column. (b) Setup screen with parameters specified for automated operation.

FIG. 10A-C are photographs of various embodiments of the present application: (a) Mounting hardware before assembly of most of fluidic and electrical system; (b) Final assembly; (c) Final assembly plus enclosure in lead.

FIG. 11A-B are tables of assignments of analog (a) and digital (b) I/O (input/output).

DETAILED DESCRIPTION OF THE INVENTION

Figure 1A:
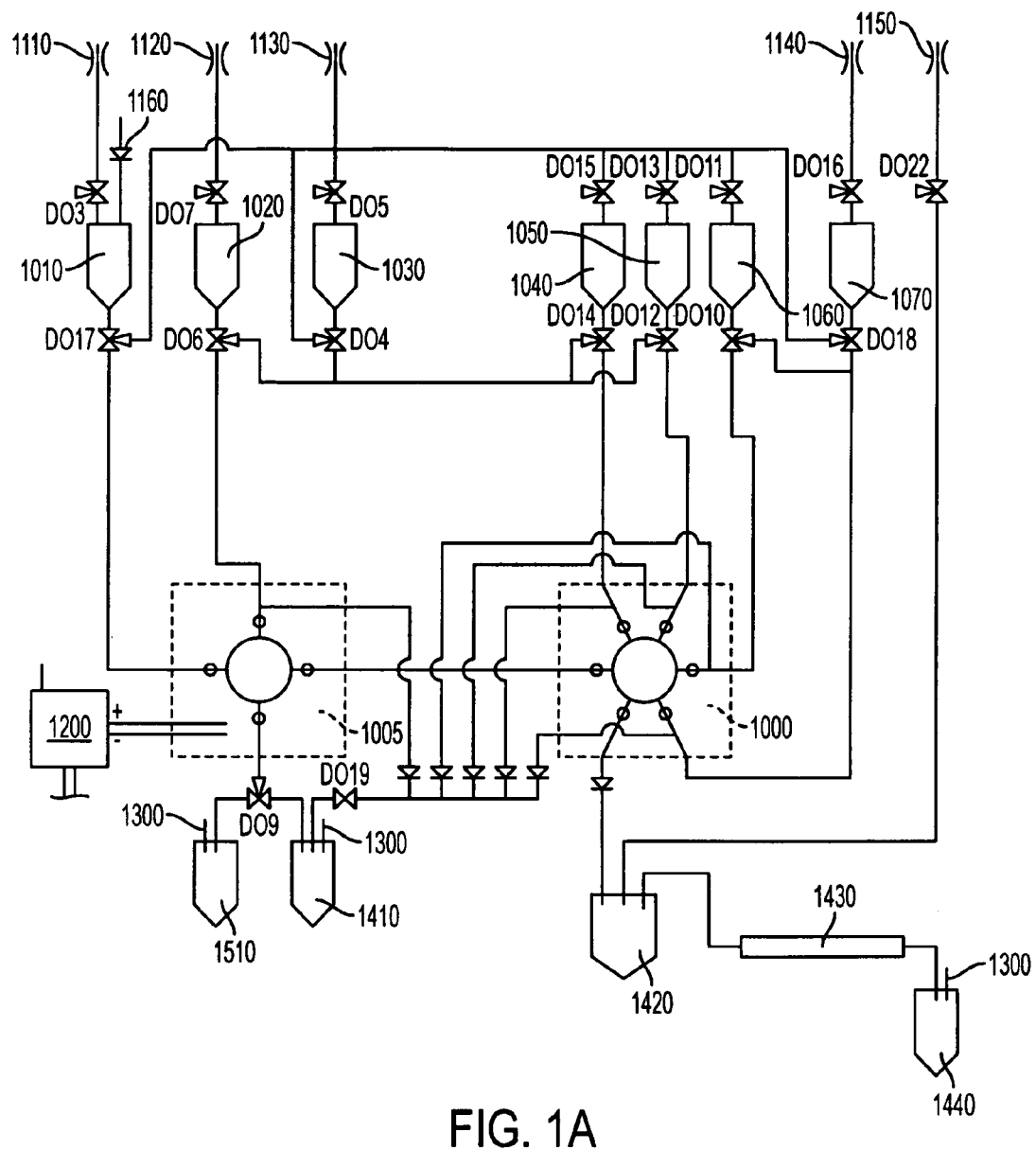
FIG. 1A-C are diagrams of an overall chemical process of one representative system of the present application: (a) fluidic pathways; (b) configuration of a temperature control system and vacuum control system and (c) a vacuum evaporation system.

Generally, conventional automated synthesizers for synthesizing radiopharmaceutical are inefficient and efficient microfluidic reactors identified so far require manual operation. The present application allows automatic operation of microfluidic reactors. Previous microfluidic reactors have been operated inside stationary leaded hot cells by a variety of mechanical, pneumatic or very simple electronic controls, requiring operator attention at all times; these reactors demonstrate notable variability as a result. The automation enabled by one aspect of this invention makes the microfluidic device autonomous and portable. In one aspect, the microfluidic system of the present application can be used in either clinical or R&D setting by medical personnel and does not require the constant presence of an engineer or specially trained operator. In another aspect of the present invention, the microfluidic system allows various steps of the synthesis to take place in a controlled traceable manner. One aspect of the application relies on pneumatic delivery of fluids with metering provided by the fixed volume of the reaction chamber with a membrane, and uses timing for various steps as the indication of their completion. In an alternative aspect of the present application, syringe drivers can be used to deliver and meter reagents more precisely. Generally, sensors can be used to monitor step completion such as, for example, solvent evaporation. This arrangement can lead to a faster and more fail-safe instrument.

In particular, the present application discloses a microfluidic system for the fully-automated synthesis of biomarkers, or radiolabeled pharmaceuticals, for positron emission tomography. This application discloses improvements on current state-of-the-art automated systems for macroscopic scale synthesis of such radiolabeled compounds due to advantages of microfluidic components. These advantages include reduced reagent use (thus reduced cost of chemical product); increased concentration of the radiolabel, such as F-18, which drives up reaction efficiencies and yields; and the ability to synthesize compounds on demand and in a flexible manner.

The presently disclosed system can contain mechanisms to add additional reagent modules, waste modules, and synthesis modules to allow the system to be used for different biomarkers from one run to the next or even simultaneously. In cases when different biomarker syntheses involve the same number of steps, the instrument may even be reused without hardware modifications. It can also be envisioned with single-use cartridges pre-loaded with reagents and/or solvents for a single run. This ease of use enables tremendous flexibility in a research environment or in specialized clinical situations where on-demand synthesis of biomarkers is needed, such as when several patients in the same day require different scans performed with different biomarkers.

In one aspect, the present application provides an automated instrument that is easy to use and flexible. In this way, the system enables non-experts to synthesize a variety of PET biomarkers on demand for biomarker development, synthesis-optimization, and testing. In another aspect, the present application provides an instrument that can be deployed in hospitals further from cyclotrons than is currently possible. The presently disclosed devices enable synthesis of fresh product on demand as contrasted to the decayed product that would arrive after a long delivery time from a centralized synthesis facility. This type of on-site instrument would greatly expand the accessibility of PET scanning to additional clinics, patients, and research labs and provide them with flexibility in the biomarkers they use that goes beyond what is available from the local radio-pharmacy.

A number of components disclosed herein have been described previously: "Microfluidic method and structure with an elastomeric gas-permeable gasket" (U.S. Ser. No. 11/701,917); "Method and Apparatus for the Mechanical Actuation of Valves in Fluidic Devices" (U.S. Ser. No. 11/514,396), and "System and Method for Interfacing with a Microfluidic Chip" (U.S. Ser. No. 11/862,167). Each reference cited herein is incorporated herein in its entirety.

DEFINITIONS

Unless specifically noted otherwise herein, the definitions of the terms used are standard definitions used in the art of organic synthesis, engineering and pharmaceutical sciences.

As used herein, a "microfluidic device" or "microfluidic chip" or "synthesis chip" or "chip" is a unit or device that permits the manipulation and transfer of microliters or nanoliters of liquid into a substrate comprising micro-channels. The device is configured to allow the manipulation of liquids, including reagents and solvents, to be transferred or conveyed within the micro channels and reaction chamber using mechanical or non-mechanical pumps. The device may be constructed using micro-electromechanical fabrication methods as known in the art. Examples of substrates for forming the device include glass, quartz or polymer. Such polymers may include PMMA (polymethylmethacrylate), PC (polycarbonate), PDMS (polydimethylsiloxane), DCPD (polydicyclopentadiene) and the like. Such device may comprise columns, pumps, mixers, valves and the like. Generally, the microfluidic channels or tubes (referred to as micro-channels or capillaries herein) have at least one cross-sectional dimension (e.g., height, width, depth, diameter) from about 1 to about 1,000 µm, alternately from about 1 to about 500 µm, or even from about 10 to about 500 µm. The micro-channels make it possible to manipulate extremely small volumes of liquid on the order of nL to µL. The micro reactors may also comprise one or more reservoirs in fluid communication with one or more of the micro-channels, each reservoir typically having a volume of about 5 to about 1,000 µL.

As used herein "reaction chamber" or "reactor" or "microreactor" refers to a cylindrical feature on the microfluidic chip (such as described here or for example in U.S. Ser. No. 11/514,396, U.S. Ser. No. 11/540,344, or U.S. Ser. No. 11/701,917, each of which is incorporated herein in its entirety by reference) where the reactions may take place. The reaction chamber has one or more micro-channels connected to it that deliver reagents and/or solvents or are designed for product removal (controlled by on-chip valves). Generally the reaction chamber has a height diameter to height with a ratio of greater than about 3, greater than about 5, greater than about 10 or more. The reactor height may be about 25 micrometer to about 1,000 micrometers. The reactor may have a diameter from about 1,000 to about 20,000 micrometers.

As used herein, "column" means a device that may be used to separate, purify or concentrate reactants or products. Such columns are well known in the art, and include ion exchange and affinity chromatography columns.

A "flow channel" or "channel" means a microfluidic channel through which a fluid or solution may flow. As is known in the art, such channels may have a cross section of less than about 1 mm, less than about 0.5 mm, less than about 0.3 mm, or less than about 0.1 mm. The flow channels of the present application may also have a cross section dimension in the range of about 0.05 microns to about 1,000 microns, or 0.5 microns to about 500 microns, or about 10 microns to about 300 microns. The particular shape and size of the flow channels will depend on the particular application required for the reaction process, including the desired throughput, and may be configured and sized according to the desired application.

"Target water" is [$^{18}$O] $H_2O$ after bombardment with high-energy protons in a particle accelerator, such as a cyclotron; it contains [$^{18}$F]fluoride. In one embodiment of the present application, preparation of target water is contemplated separately from the system disclosed herein. In one embodiment of the present application, target water is supplied to the system from a cartridge; in another embodiment, from a pre-filled individual vial.

A microfluidic "valve" (or "micro-valve") as used herein, means a device that may be controlled or actuated to control or regulate fluid or solution flow among various components of the microfluidic device, including flow between flow channels, solvent or reagent reservoirs, reaction chamber, columns, manifold, temperature controlling elements and devices, and the like. Such valves are known in the art and include, for example, mechanical (or micromechanical valves), (pressure activated) elastomeric valves, pneumatic valves, solid-state valves, etc. Examples of such valves and their method of fabrication may be found, for example, in "The New Generation of Microvalves" *Analytical Chemistry*, Felton, 429-432 (2003).

As used herein, the term "radioactive isotope" refers to isotopes exhibiting radioactive decay (i.e., emitting positrons). Such isotopes are also referred to in the art as radioisotopes or radionuclides. Radioactive isotopes are named herein using various commonly used combinations of the name or symbol of the element and its mass number (e.g., $^{18}$F, [F-18], fluorine-18). Exemplary radioactive isotopes include I-124, F-18, C-11, N-13, and O-15, which have half-lives of 4.2 days, 110 minutes, 20 minutes, 10 minutes, and 2 minutes, respectively.

The term "reactive precursor" or "precursor" refers to an organic or inorganic non-radioactive molecule that is reacted with a radioactive isotope, typically by nucleophilic substitution, electrophilic substitution, or ionic exchange, to form the radiopharmaceutical. The chemical nature of the reactive precursor depends upon the physiological process to be studied. Typically, the reactive precursor is used to produce a radiolabeled compound that selectively labels target sites in the body, including the brain, meaning the compound can be reactive with target sites in the subject and, where necessary, capable of transport across the blood-brain barrier. Exemplary organic reactive precursors include sugars, amino acids, proteins, nucleosides, nucleotides, small molecule pharmaceuticals, and derivatives thereof. One common precursor used in the preparation of $^{18}$F-FDG is 1,3,4,6-tetra-O-acetyl-2-O-trifluoromethanesulfonyl-β-D-mannopyranose.

As used herein, the phrase "reactor temperature" refers to a temperature observed and/or maintained in the reaction chamber.

As used herein, "reaction time" refers to the time allowed for a reaction to run before the next step takes place.

The phrase "reagent pressure" or "solvent pressure" refers to the pressure of a gas (usually an inert gas such as nitrogen or argon) applied to a reagent or solvent vial that drives a reagent or solvent into a flow channel, e.g. on the way to the reaction chamber.

The phrase "time of reagent filling" or "time of solvent filling" refers to the time allowed for a reagent or solvent to enter the microfluidic chip before the on-chip valve closes, thereby inhibiting passage of additional reagent or solvent onto the chip.

The term "evaporation" refers to the change in state of solvent from liquid to gas and removal of that gas from the reactor. Generally gas is removed by vacuum applied across the membrane. Various solvents are evaporated during the synthetic route disclosed herein, such as for example acetonitrile and water. As known to those of skill in the art, each solvent, such as acetonitrile and water, may have a different evaporation time and/or temperature.

The term "elution" generally refers to removal of a compound from a particular location. Elution of [F-18]fluoride from the ion exchange column refers to the conveyance of [F-18]fluoride by the eluting solution from the column to the reaction chamber. Elution of product from the reaction chamber refers to conveyance of the product from the reaction chamber to the off-chip product vial by flushing the reaction chamber with a volume of solvent, e.g. water.

The "off/on time" in reference to the vacuum applied at a point in the system refers to the point in time of the radiosynthesis operation when the vacuum is turned on or off.

"Inert gas pressure," including "nitrogen pressure" or "argon pressure" refers to pressure of inert gas, such as nitrogen or argon, allowed past a given regulator.

The phrase "internal filter" refers to a vial, a syringe or another container that is filled with absorbent material such as charcoal and comprises two ports. When the exhaust from the microfluidic chip is passed through such a filter, radioactive and non-radioactive contaminants are generally caught by and stay on the filter. After passage of the reaction exhaust through an internal filter purified gas is released into the atmosphere. Use of an appropriate internal filter reduces or even eliminates the need for an additional exhaust processing for safe operation of the portable system. In one embodiment, it is not necessary to operate the portable system disclosed herein in a fume hood.

The term "priming" when used in reference to a reagent flow channel refers to conveying a reagent through the flow channel connecting the reagent source and the reaction chamber, wherein the reagent flow passes a closed on-chip valve and flows via an open flow channel to a waste receptacle. In this fashion, when the reagent is to be added to the reaction chamber, the corresponding on-chip valve is opened and pneumatic actuation conveys the reagent from the primed flow channel into the reaction chamber with minimal delay. In the alternative when a flow channel is not primed, the reagent must travel the length of the flow channel from the reagent source to the reaction chamber, displacing the gas in that path through the gas-permeable membrane on the synthesis chip. Displacing a significant amount of gas through the gas permeable membrane on the synthesis chip can put a strain on the system, which is avoided by priming the flow channel. Analogously, when appropriate, the term 'priming' can be used in reference to a solvent flow channel.

The phase "pre-packaged disposable reagent cartridge" refers to an apparatus designed to fit removably and interchangeably into or onto an automated system described herein; where the apparatus contains one or more separate reagent sources. The reagent(s) held within the cartridge, after fitting the cartridge into the system described herein, can be conveyed to the reaction chamber as described herein via pneumatic delivery. When appropriate for the preparation of a radiolabeled compound, the reagent cartridge can contain solvents as well as reagents. Alternately, solvents can be provided separately from the reagents.

In one embodiment, automated systems disclosed herein include those which comprise a disposable reagent cartridge. In one embodiment, the present application discloses an automated system with the flexibility to make a variety of different radiopharmaceuticals with minimal risk of cross-contamination, by simply changing the cartridge. Using such a cartridge has a number of advantages including simplified set-up; rapid change between production runs; pre-run automated diagnostic checking of the cartridge and reagents; reagent traceability; single-use, tamper and abuse resistance. Substitution of a reagent cartridge eliminates the need to design an entirely new automated synthetic system each time a different radiopharmaceutical is to be prepared.

Suitable heat sources for use in the synthetic systems disclosed herein include but are not limited to resistive heating, localized and non-localized microwave heating and Peltier devices. Various sensors (e.g., flow sensors, radioactivity sensors, pressure sensors, temperature sensors, and the like) and other apparatus components (e.g., valves, switches, etc.) can be integrated into the system and connected to a computer for process control and monitoring purposes.

The synthetic systems disclosed herein comprise a microfluidic synthesis chip in which, for example, reagents are mixed and heated, solvents are exchanged, etc to carry out the desired chemical process.

FIG. 1 shows a flow diagram in an overall process in one embodiment of the presently disclosed system. FIG. 1a in particular displays the fluidic pathways, particularly in the synthesis of [F-18]FDG, in which delivery of each reagent and solvent is controlled by the pressure of an inert gas pressurizing each reagent or solvent vial. In the figure, the location of various valves, including 2-way, 3-way and check valves for liquid and gas lines are identified but not explicitly described below. In the synthesis of [F-18]FDG, [F-18]/target water is conveyed along a flow channel from a cyclotron, 1160, into a [F-18]/target water vial, 1010, as controlled by an $N_2$ regulator, 1110, which also adjusts the trap chip, 1005, flow rate. Conveyance of $K222/K_2CO_3$/acetonitrile from a vial 1020, can controlled by an $N_2$ regulator, 1120, which also controls the trap elution flow rate. Delivery of solvent from an acetonitrile vial, 1030, is controlled by an $N_2$ regulator, 1130, which can also adjust the flow rate of the solvent wash process. Delivery of mannose triflate from vial 1050, of hydrochloric acid from vial 1060, and of solvent from a water vial, 1070, is controlled by an $N_2$ regulator, 1140, which can adjust the reactor elution flow rate as well. Vial 1040 is configured as an empty vial in the preparation of $^{18}$F-FDG, but can be employed in preparation of another radiopharmaceutical. Trapping of [F-18] from target water is accomplished in the disclosed trap chip, 1005, or an alternative trap/release device such as a trap cartridge. The electrochemical trapping of [F-18] is powered by a high voltage power supply, 1200, with a set point provided by an operator. $[O-18]H_2O$ can be collected from the trap chip, 1005, in a recovery vial, 1510, equipped as necessary with a vent, 1300. Waste from the trap chip, 1005, can be collected in the waste vial, 1410, also equipped with a vent, 1300. Isolated [F-18] can be conveyed to the synthesis chip, 1000. Priming of the reagent flow channels (the process of which is not shown) is enabled by the disclosed bypass lines and on-chip valves. After the reaction(s) in the reaction chamber of the synthesis chip, 1000, the radiopharmaceutical product is conveyed to a raw product receptacle, 1420, and then via $N_2$ pressure from regulator 1150 is conveyed to purification column, 1430. The targeted product is eluted to the product vial (or product receptacle), 1440, which is also equipped with a vent, 1300, as necessary.

Figure 1B:
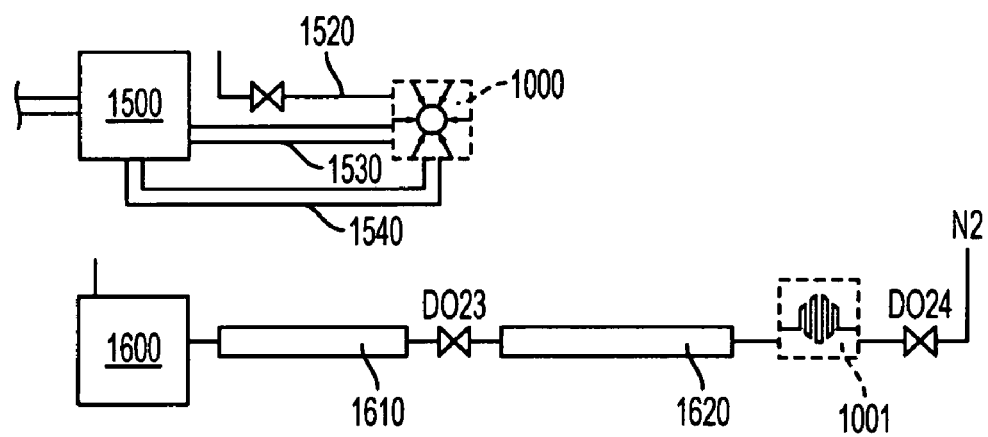
Figure 1C:
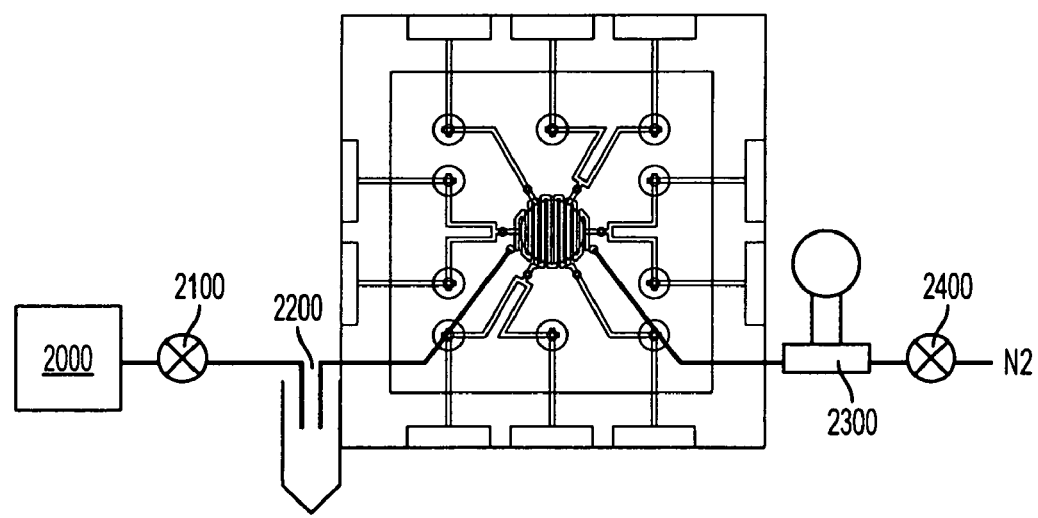

FIG. 1b displays one configuration of a temperature control system. The temperature controller, 1500, is coupled via a heater, 1530, and a thermocouple, 1540, to the synthesis chip, 1000. Air can travel through a two-way or three-way valve in the vortex cooler, 1520. FIG. 1b also displays one configuration of a pressure control system. The vacuum pump, 1600, is coupled to a vacuum trap, 1610, which is further coupled to a pressure transducer, 1620. The configuration further discloses the vent layer, 1001, of a synthesis chip, 1000. FIG. 1c displays one configuration of a vacuum evaporation system. A vacuum pump, 2000, is in communication with vacuum trap, 2200, by way of a 2-way vacuum valve, 2100. Between the synthesis chip and the nitrogen source is a vacuum trap, 2300, adjacent to a 2-way gas valve, 2400.

Figure 3:
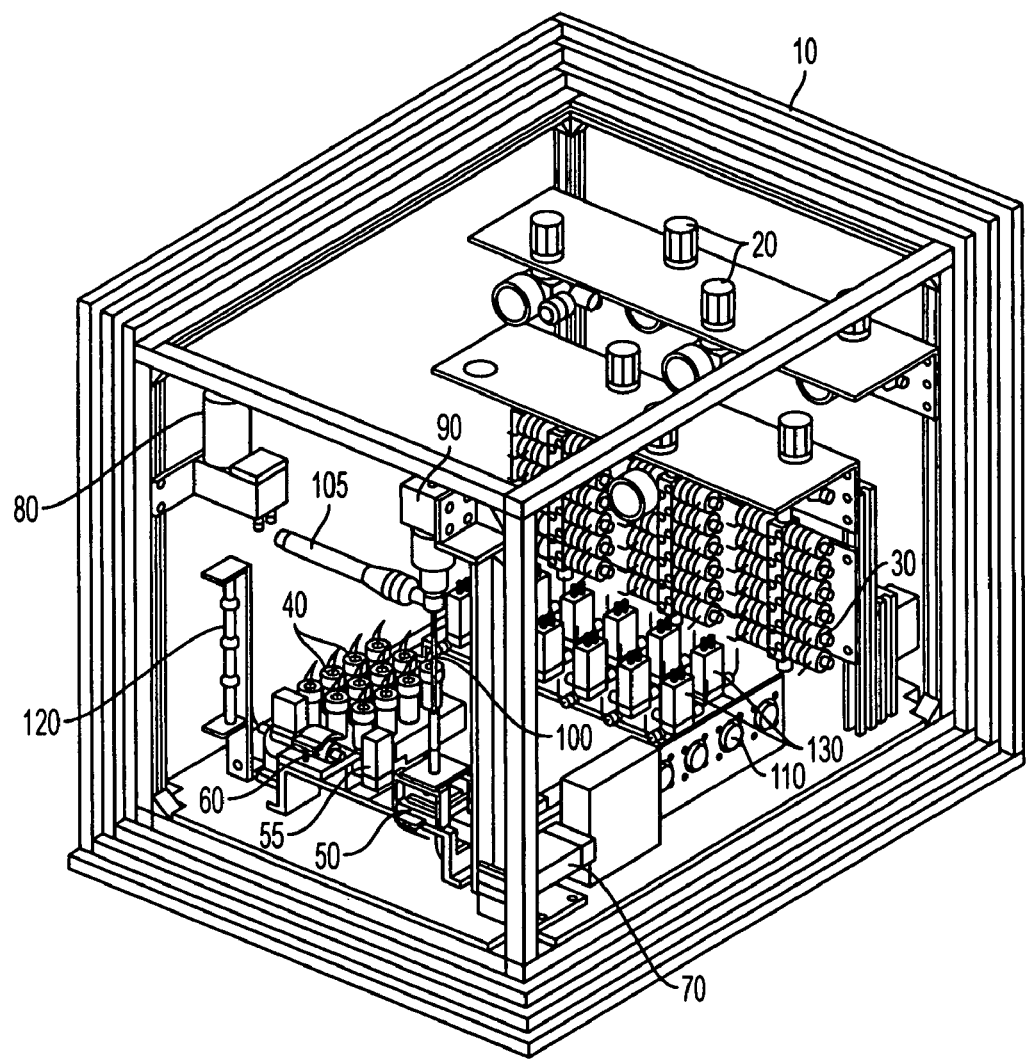
FIG. 3 is an engineering drawing of one embodiment of the present application.

FIG. 3 shows an engineering drawing of one system disclosed herein. The system is fully enclosed by a three-layer lead shield, 10. Gas pressure controls, 20, are individually attached to a single gas inlet (not shown) and to gas valves, 30. The reagents in the reagent/solvent vials, 40 (or reagent/solvent sources), are conveyed via flow channels e.g. to the synthesis chip, 50. Liquid valves, 130, are located before and after reagent vials and before waste vials and product vial(s); these valves control the entrance/exit to/from the vials for reagents, product, and waste. Access to the reaction chamber of the synthesis chip, 50, is controlled by pneumatic cylinders, 55. The radiolabel, e.g. [F-18], is isolated from target water by passage through a trapping module, such as an ion exchange column, 60 (or alternatively via electrochemical trapping). The temperature controller, 70, also comprising a temperature monitor, is operatively connected to the synthesis chip, 50. Analogously, the pressure controller (not shown) is operatively connected to the synthesis chip, 50, and to the vacuum pump, 80. In this embodiment, a camera, 90, is held above the synthesis chip, 50, in line with a borescope, 100, and in conjunction with a light source, 105, to monitor the process occurring in the reaction chamber of the synthesis chip, 50. The camera, 90, can be operatively attached to a display screen, such as a computer screen (not shown but can be seen in FIG. 10c) outside the lead shield and which can display live images collected of the synthesis chip, 50. Operation of the system is controlled by the controller (not shown) operatively connected to the system via communication ports, 110. The controller (not shown) is further connected to a computer (not shown but can be seen in FIG. 10c) at which an operator can input desired variables. The purification cartridge, 120, is in fluid communication with the synthesis chip, 50, however to simplify FIG. 3, the interconnecting flow channels are not included in this view.

Figure 4:
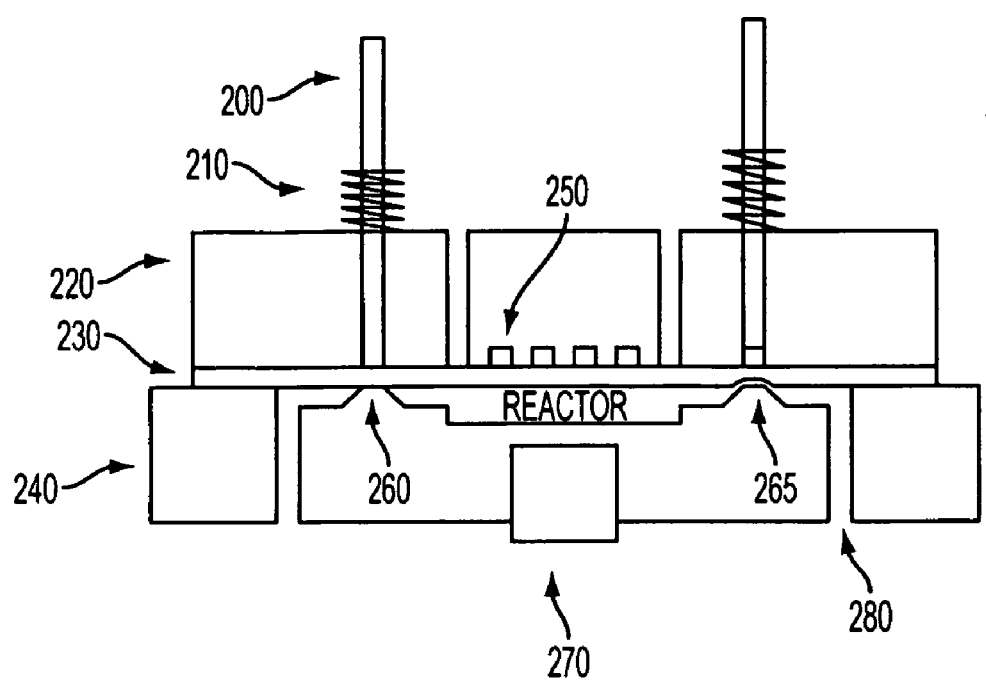
FIG. 4 is a cross-section of a microfluidic chip appropriate for use in the systems disclosed herein illustrating some of the features in each layer and a representative architecture of the on-chip diaphragm valves.

FIG. 4 shows the cross-section of one microfluidic chip appropriate for use in the present invention. The chip comprises three layers: the gasket layer, 230, between a rigid lower fluid layer, 240, and a rigid upper vent layer, 220. The fluid layer contains a reagent inlet channel, 280, as well as a heater/cooler apparatus, 270. The fluid layer in this Figure also demonstrates a closed valve, 260, and an open valve, 265. Positioned above each valve is a valve actuating rod, 200, comprising a return spring, 210. Vacuum channels, 250, are shown in the vent layer, 220.

FIG. 5 shows the fluid layer (in A) and the vent layer (in B) in a representative microfluidic chip that can be employed in the presently disclosed system. The fluid layer contains channels (300, 310, and 330) for the input of reagents such as for example, a radiolabel, e.g. F-18, 300, a precursor, 330, a deprotectant, 310, as well as a phase transfer agent, 320, and an eluent, 340. The fluid layer contains channels for the outlet of waste, 350, and for the outlet of product, 360. The vent layer contains a serpentine vacuum channel, 390, and holes, 380, to align the valve actuating rods on top of the valve seats. The vent layer further has bolt holes, 370, (also shown in the fluid layer) for bolts used to hold the layers together.

Figure 7:
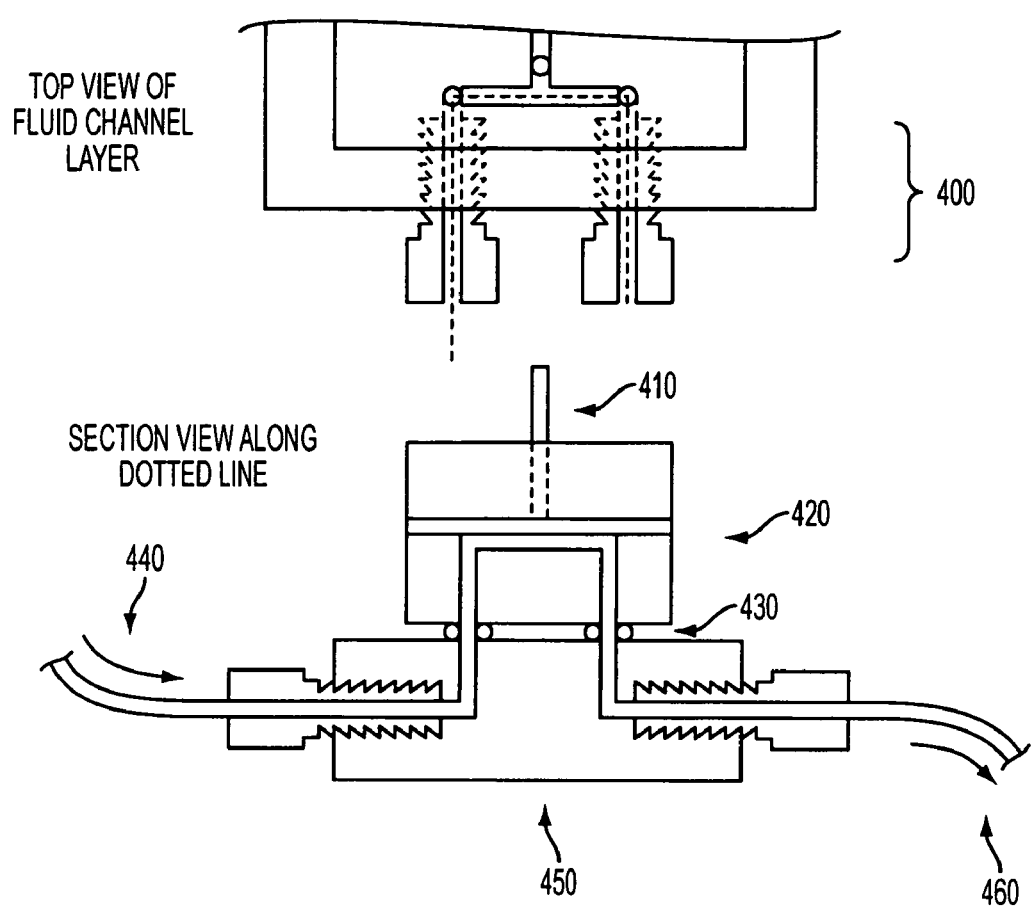
FIG. 7 discloses operation of a representative priming mechanism in the fluidic adapter interface.

FIG. 7 shows operation of a representative priming mechanism in the fluidic adapter interface. FIG. 7A shows the top view of the fluid channel layer and indicates the priming loop, 400. FIG. 7B shows the section view along the dotted line and indicates the configuration relative to the microfluidic chip, 420, and the fluidic adapter, 450, which are separated by an O-ring, 430. The reagent travels along the flow channel, 440, from the reagent source and can pass to waste along the corresponding flow channel, 460. Also shown is a valve actuating rod, 410.

Figure 8:
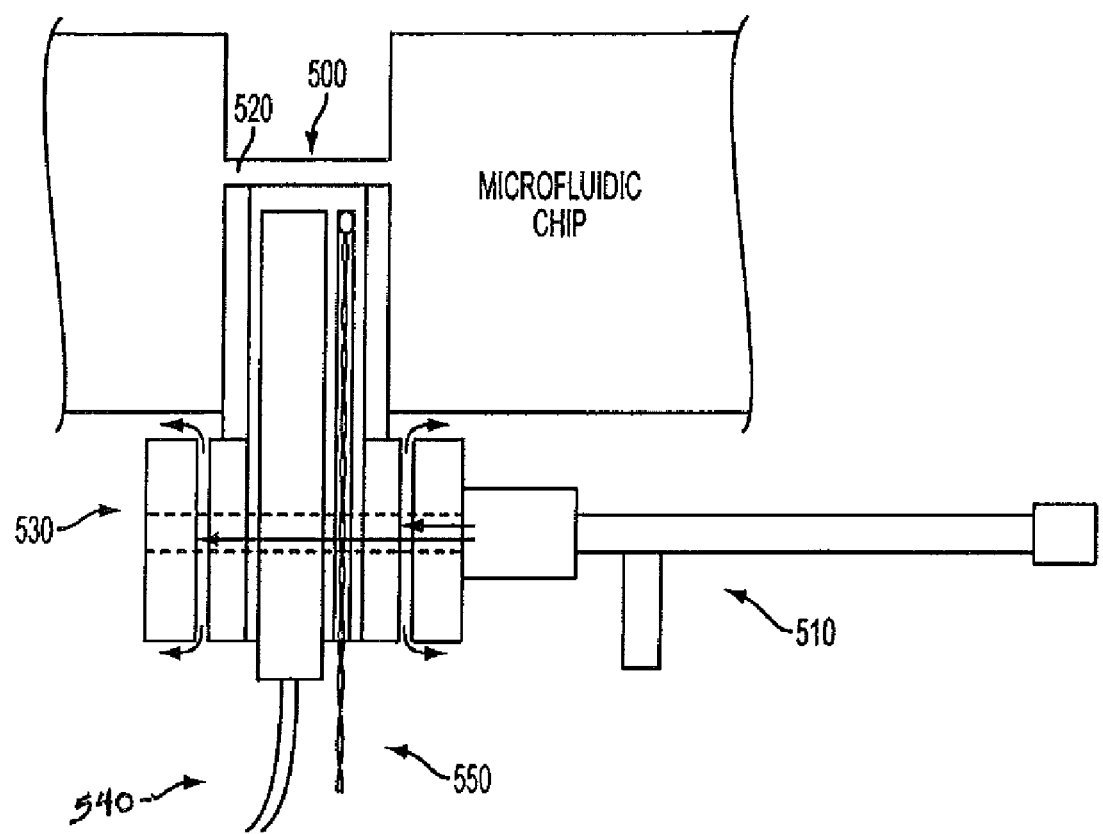
FIG. 8 is a schematic of a representative chip heating and cooling system.

FIG. 8 shows a schematic of a representative heating and cooling system for a microfluidic chip. The Figure demonstrates the orientation of the reaction chamber, 500, relative to a temperature control base, 530, a cartridge heater, 540, and thermocouple, 550. One configuration of a vortex cooler, 510 is also shown, as is the arrangement of insulation, 520.

Figure 9:
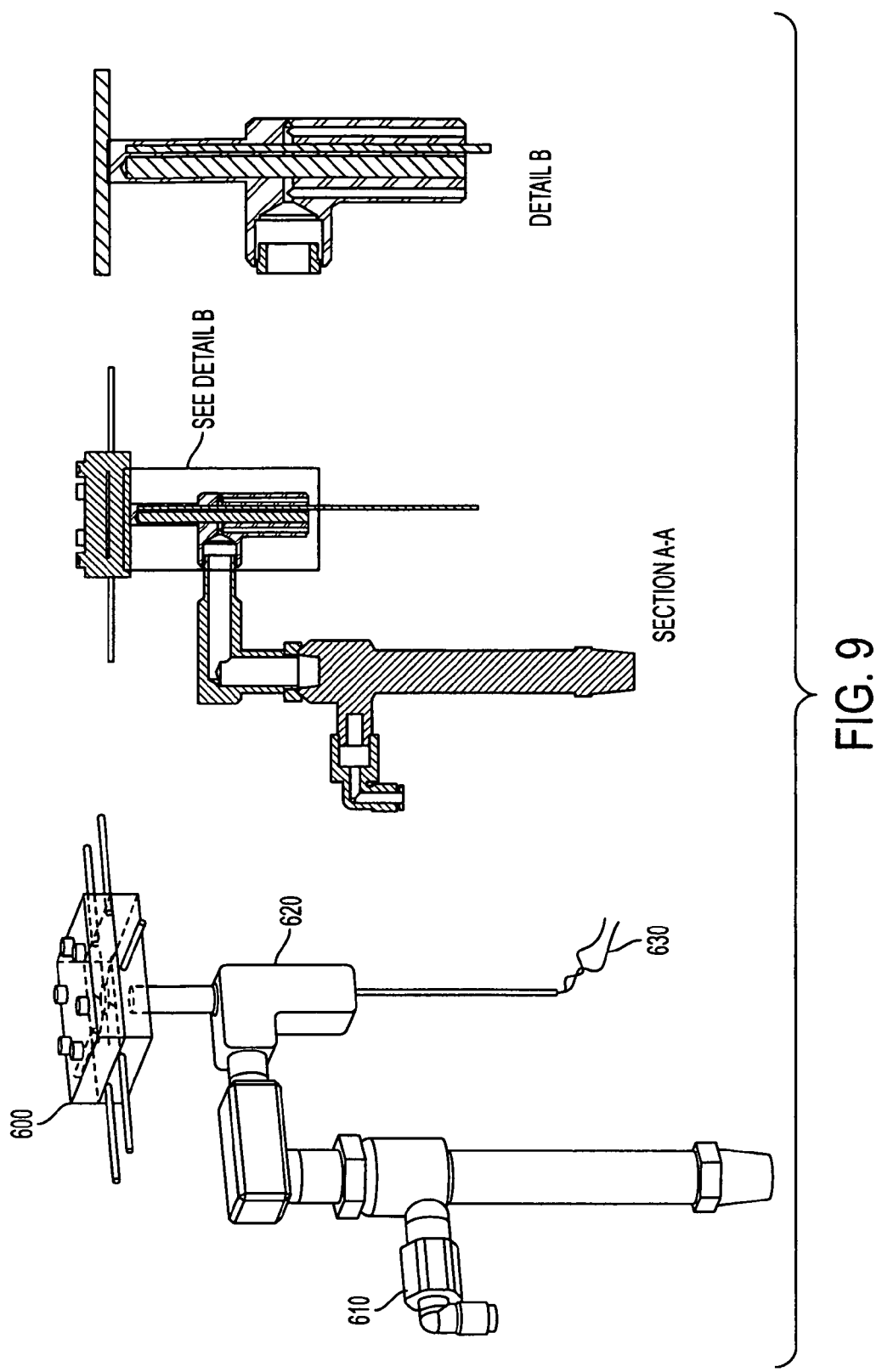
FIG. 9 is an engineering drawing of a representative heater and cooler assembly.
Figures 6, 11B:
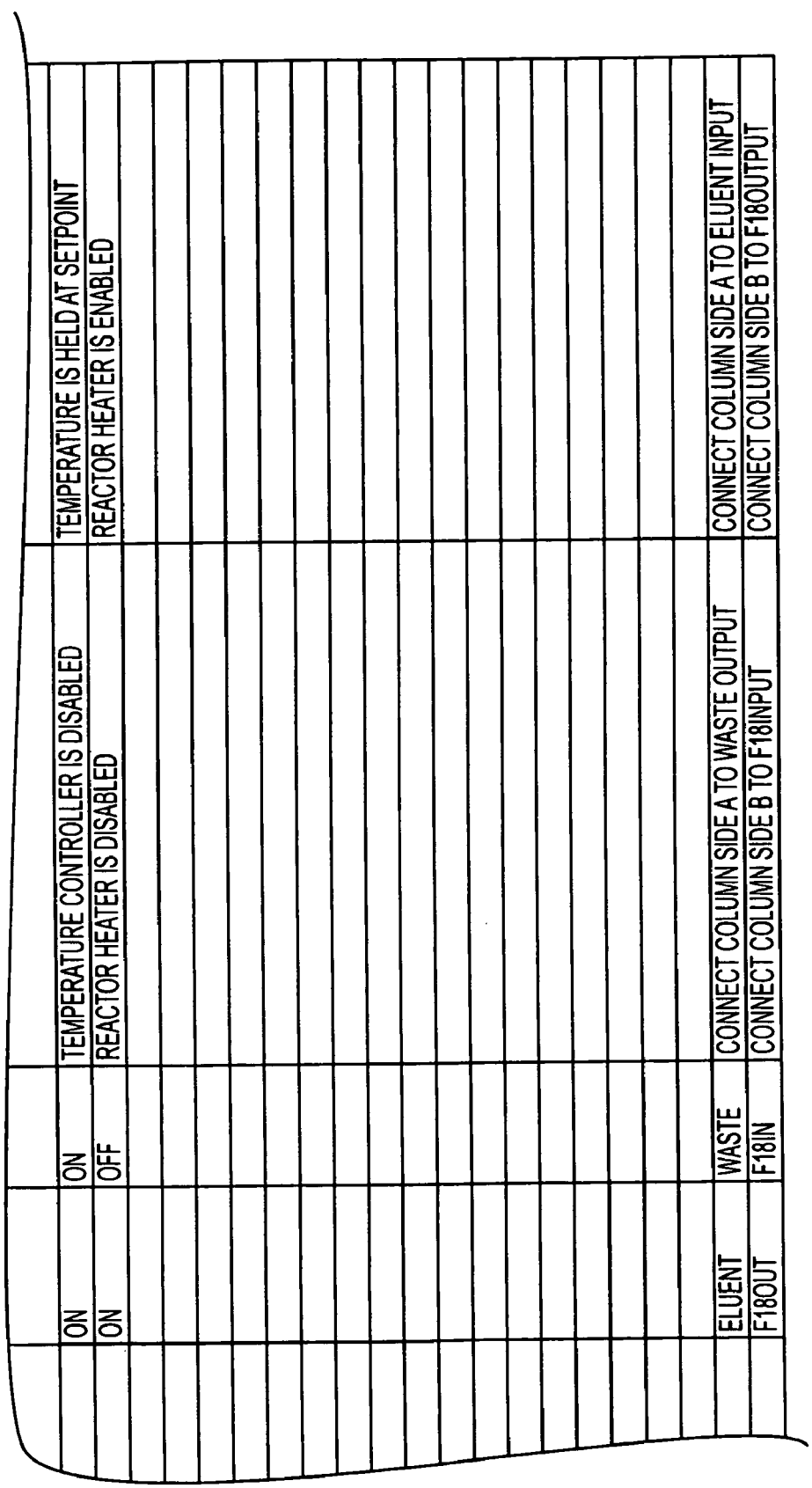

FIG. 9 is an engineer drawing of a representative heater and cooler assembly relative to a microfluidic chip, 600, showing a possible arrangement of a thermocouple, 630, a heating/cooling block, 620, and a vortex cooler, 610.

Aspects, Embodiments, and Variations:

The present application provides the following embodiments, aspects and variations:

One aspect of the application is a portable system for the automated radiosynthesis of a radiolabeled compound comprising:

a microfluidic synthesis chip comprising a reaction chamber of fixed volume, a membrane, at least one flow channel and at least one valve;

a reagent source comprising at least one reagent in fluid communication via a flow channel with the synthesis chip, wherein the reagent is conveyed in a metered amount to the reaction chamber via pneumatic actuation; and at least one external input device coupled to at least one controller which is coupled to and controls the function of at least one component selected from the group consisting of an inert gas delivery source, a vacuum system, a temperature control system and a valve on the synthesis chip.

In one embodiment, the system is further configured for priming the flow channel, wherein the priming comprises conveying the reagent from the reagent source to the valve on the synthesis chip, wherein the valve is closed and the reagent is conveyed to a waste receptacle in fluid communication thereto.

In another embodiment, the reagent is conveyed from a pre-filled individual vial or from a pre-packaged cartridge.

In yet another embodiment, the system further comprises radiation shielding. In one variation, the system does not require a separate hot cell. In another variation the radiation shielding shields one or more of:

a) a radiolabel source in fluid communication via a flow channel with the reaction chamber;

b) the flow channel of the radiolabel source;

c) the synthesis chip;

d) a purification system in fluid communication with the synthesis chip; and e) a product receptacle in fluid communication with the purification system.

In another embodiment, the system further comprises a heat-exchanger. In one variation the heat-exchanger heats the reaction chamber via a resistive heater and cools the reaction chamber by air in a vortex cooler.

In one embodiment, the radiolabeled compound is radiolabeled with F-18, C-11, N-13, O-15 or I-124. In one embodiment, the radiolabeled compound is radiolabeled with C-11. In one variation, the radiolabeled compound is radiolabeled with F-18. In another variation, radiolabeled compound is selected from the group consisting of: 2 deoxy-2-[F-18]-fluoro-D-glucose ($^{18}$F-FDG), 3'-deoxy-3'-[F-18]-fluorothymidine ($^{18}$F-FLT), 9 [4-[F-18] fluoro-3-(hydroxymethyl)butyl]guanine ($^{18}$F-FHBG), 9-[(3-[F-18] fluoro-1-hydroxy-2-propoxy)methyl]guanine ($^{18}$F-FHPG), 3-(2'-[F-18] fluoroethyl)spiperone ($^{18}$F-FESP), 4-[F-18] fluoro-N-[2-[1-(2-methoxyphenyl)-1-piperazinyl]ethyl]-N-2-pyridinyl-benzamide ($^{18}$F-p-MPPF), 2(1{6[(2[F 18]fluoroethyl)-(methyl) amino]-2-naphthyl}ethylidine)-malononitrile ($^{18}$F-FDDNP), 2-[F-18] fluoro-α-methyltyrosine, [F-18] fluoromisonidazole ($^{18}$F-FMISO), and 5-[F-18] fluoro-2'-deoxyuridine ($^{18}$F-FdUrd). Alternately, the radiolabeled compound is selected from the group consisting of: 2 deoxy-2-[F-18]-fluoro-D-glucose ($^{18}$F-FDG), 3'-deoxy-3'-[F-18]-fluorothymidine ($^{18}$F-FLT), and 2(1-{6-[(2-[F-18]fluoroethyl)-(methyl)amino]-2-naphthyl}ethylidine)malononitrile ($^{18}$F-FDDNP).

In one embodiment, the radiolabeled compound can be 2 deoxy-2-[F-18]-fluoro-D-glucose ([F-18]FDG). In one variation, one reagent is target water, [O-18]H$_2$O containing [F-18], and isolation of [F-18] from target water relies on electrochemical trapping. In another embodiment, isolation of [F-18] from the target water relies on an ion-exchange column. In one variation, the concentration of the [F-18]FDG is at least about 100 times that of the concentration of F-18 in target water. In yet another embodiment, the instrument can achieve 200-fold concentration of F-18 from target water, in contrast to conventional methods that rely on about 5-fold concentration. In another embodiment, the instrument achieves 300-fold concentration; and in a yet another embodiment, in the concentration of the F-18 radiolabeled compound is at least about 400 times that of the concentration of F-18 in the target water.

In one embodiment, the flow channel connecting the reagent source with the synthesis chip further comprises a check valve and/or a 3-way valve. In one variation, the system further comprises an inert gas inlet wherein the system is pressurized by inert gas from the inlet and the speed with which the reagents are conveyed from the source to the reaction chamber is controlled by pressure of an inert gas. In another variation, the inert gas is split into various pressures.

In yet another variation, the speed with which the reagents are conveyed from the reagent source to the reaction chamber is controlled by the thickness and/or composition of the membrane.

In one embodiment, the system can be cleaned without requiring disassembly of the system, wherein the cleaning step comprises conveying a solvent from a solvent source via a flow channel through the reaction chamber to a waste receptacle and optionally conveying an inert gas from the inert gas delivery source through the reaction chamber.

In one embodiment, the radiolabeled compound is collected in a product vial, wherein the product vial is shielded from the microfluidic synthesis chip and/or the reagent source.

In another embodiment, the vacuum system comprises pump, a trap, a valve and an electronic pressure gauge readable by the external input device. In another embodiment, the system further comprises a pressure controller.

In yet a further embodiment, the system comprises at least one internal filter. In one variation, the system can safely operate outside a fume hood. In another variation, the purification system comprises a column.

In another embodiment, the radiolabeled compound is formed via a process occurring in the reaction chamber and is conveyed to a purification system via pneumatic actuation. In one variation, the process in the reaction chamber is monitored using a borescope inserted through an actuation plate positioned adjacent to the microfluidic device.

In one embodiment, the at least one controller controls the function of an inert gas delivery source, a vacuum system, a temperature control system and a valve on the synthesis chip.

Another aspect of the present application is a portable system for the automated radiosynthesis of a radiolabeled compound comprising:

a microfluidic synthesis chip comprising a reaction chamber of fixed volume, a membrane, at least one flow channel and at least one valve;

a reagent source comprising at least one reagent in fluid communication via a flow channel with the synthesis chip, wherein the reagent is conveyed in a metered amount to the reaction chamber via pneumatic actuation;

radiation shielding;

a heat-exchanger, wherein the heat-exchanger heats the reaction chamber via a resistive heater and cools the reaction chamber by air in a vortex cooler at least one external input device coupled to at least one controller which is coupled to and controls the function of at least one component selected from the group consisting of an inert gas delivery source, a vacuum system, a temperature control system and the valve on the synthesis chip. In one embodiment, the system further comprises off-chip liquid and gas valves.

Another aspect of the present application is a method for the synthesis of purified [F-18]-FDG comprising the use of the system of claim 1 wherein one reagent is target water, [O-18]$H_2O$ containing F-18, one solvent is water and the [F-18]FDG is collected in a product receptacle. In one embodiment, an operator inputs into the external input device a value for one or more variables selected from the group consisting of: reactor temperature, reaction time, reagent pressure, times of reagent filling, evaporation, elution; vacuum on/off time, and inert gas pressure. In another embodiment, the operator inputs into the external input device the value before implementation of the system and does not input another value into the external input device at least until the radiolabeled compound is synthesized. In yet another embodiment, an operator inputs into the external input device a value for each of reactor temperature, reaction time, reagent pressure, times of reagent filling, evaporation, elution; vacuum on/off time, and inert gas pressure. In still another embodiment, the operator inputs into the external input device each of the values before implementation of the system and does not input another value into the external input device at least until the radiolabeled compound is synthesized. In one variation, the method further comprises removing [F-18]FDG from the system; cleaning the system with water and drying the system with an inert gas.

Another aspect of the present application is a machine-readable computer program code, the program code including instructions for causing a controller to implement a method for the synthesis system of claim 1, for method comprising:

introducing one or more reagents into for reaction chamber;

operating the synthesis system to process the reagent(s) responsive to a predetermined algorithm to generate a radiolabeled compound; and collecting for radiolabeled compound.

In one embodiment, the algorithm includes parameters for one or more variables selected from the group of reactor temperature, reaction time, reagent pressure, times of reagent filling, evaporation, elution; vacuum on/off time, and inert gas pressure. In another embodiment, the algorithm includes parameters for each of the variables: reactor temperature, reaction time, reagent pressure, times of reagent filling, evaporation, elution; vacuum on/off time, and nitrogen pressure. In one variation, at least one parameter is input before implementation of the synthesis system. In another variation, the machine-readable computer program code is encoded onto a storage medium.

In one embodiment, each reagent and/or solvent is delivered to the synthesis chip from an individual reagent/solvent source. In such an example, each reagent/solvent source may have two ports into which tubing is inserted: an inlet and an outlet. The inlet tubing sits above the fluid surface and is in fluid communication with an electronically controlled 3-way valve connected to a pressurized inert gas supply (e.g. $N_2$ or argon). In one embodiment, each reagent/solvent has its own individually-controllable pressure, to allow flexibility by allowing different flow rates. The outlet line (or outlet channel) of each reagent/solvent source can be a piece of tubing with one end at the bottom of the reagent vial and heading toward the microfluidic chip. The 3-way valve connected to the inlet can be opened such that the reagent/solvent vial is pressurized and the reagent/solvent is pushed into the outlet line, or it can be vented such that the reagent/solvent vial is open to atmosphere and depressurized.

Most lines (or channels) from reagent/solvent vials pass through an additional electronically-controlled 3-way valve on the way to the synthesis chip so that a "wash" solvent and/or inert gas (nitrogen or argon) can be directed toward the synthesis chip to clean and dry one or more lines at the end of a synthesis run. Drying the lines helps to avoid liquid leaks when removing and reinstalling the chip from the interface adapter. Drying also helps avoid contamination of subsequent runs with previously run components or dilution of reagents by cleaning solvents. In addition, check valves are placed in the inlet lines on the way to the synthesis chip to ensure no back flow into a reagent/solvent vial should there be any leaky microfluidic chip valves (or valves switched inadvertently at an incorrect time).

In one embodiment the reagents/solvents are loaded individually in pre-filled vials into the system. In another embodiment, these reagents/solvents can be packaged into a single reagent cartridge that can be installed in one step, or could be packaged in tiny quantities with each synthesis chip to easily allow the synthesis of different biomarkers. A different set of reagents/solvents and possibly different chip configuration could then be used for each desired radiosynthesis.

In one exemplary system, the radiolabel, such as F-18, is delivered from a cyclotron through a check valve and into a temporary storage vial inside the instrument. In a another exemplary system, the radiolabel is delivered each day in an easy-to-connect leaded-vial or possibly in the solid-phase (e.g. attached to an ion-exchange column to be eluted into a temporary storage vial inside the instrument). It is not anticipated that operators will have their own cyclotron and delivery as necessary, e.g. daily, of the radioactive label addresses this deficiency. In one example of [F-18]FDG synthesis, F-18 is provided in a solution of target water: the solution is first passed through an exchange resin to trap and concentrate F-18; the F-18 is then eluted into the microfluidic synthesis chip using a $K_2CO_3$ solution. To minimize the fluid volume transferred from the exchange column to the microfluidic synthesis chip, an ultra-low volume (0.5 µL) rotary valve is used in this part of the fluidic system.

Other methods of trapping fluoride ion (e.g. electrochemical trapping, such as is disclosed in U.S. Ser. No. 60/950,976 "Microfluidic Radiosynthesis device relying on electrochemical trapping and release of F-18 in its isotope concentration step") can alternatively be easily integrated into the system. With electrochemical trapping, the controller, and by extension the computer can additionally control the high voltage supply necessary in this setup.

The radiolabeled product made in the synthesis chip is eluted with solvent through a purification system, such as, for example, a column, and into the final collection vial (or product receptacle) and is diluted to the volume required for analysis and/or injection into the patient. In one embodiment, the product receptacle is located in a leaded vial or syringe affixed to the outside of the instrument for easy and quick removal and delivery to the patient or for further analysis.

In the pathway of a solvent, such as e.g. water, to the microfluidic synthesis chip can be found an additional electronically-controlled 3-way valve. In one position, this valves allows solvent to flow into the synthesis chip. In the other configuration, it allows liquid to come from the synthesis chip and flow to waste. This valve is used during the wash/clean phase. Wash solvents and gas ($N_2$ or argon) are flowed through the synthesis chip to drain and clean it. In one embodiment, the system can be washed with solvent without disassembling the system.

The automated system also controls the valves integrated in the microfluidic gasket chip. Pneumatic pistons that drive the mechanical actuating pins in these valves are driven by compressed air (or another gas) that is controlled by electronic valves on demand. Examples of placement and operation of pneumatic valves are disclosed in FIGS. 1 and 4.

A number of synthesizers known in the art employ gas pressure actuated elastomeric valves or pneumatic valves. In addition, there is significant literature disclosing the control of microfluidic valves by various methods of actuation. See for example, U.S. 2002/0127736 "Microfluidic devices and methods of use," incorporated herein in its entirety by reference. In one aspect, the microfluidic devices disclosed in the present application employ mechanical valves [such as presented in U.S. 2007/0051412, incorporated herein in its entirety by reference] that are capable of operating efficiently under high pressures. The design of the microfluidic device disclosed accomplishes these and other objectives as disclosed herein.

Details of a microfluidic chip, and reagent delivery via a dead-volume bypass mechanism which can be incorporated into the presently disclosed system are discussed in U.S. Ser. No. 11/862,167 "System and Method for Interfacing with a Microfluidic Chip," incorporated herein in its entirety by reference.

In one embodiment, the microfluidic synthesis chip contains a closed "coin-shaped" reactor surrounded by six channels and valves for flow of reagents and product. The reactor can be heated to facilitate reactions and solvents can be exchanged by evaporating across the gas-permeable membrane in the ceiling of the reactor then refilling with the next reagent in the new solvent.

In one aspect the presently disclosed system comprises a synthesis chip is fabricated from three layers—a flexible "gasket layer" between a rigid lower "fluid layer" and a rigid upper "vent layer" (see FIG. 4). These layers can be held together by bolts rather than chemical adhesion, which simplifies fabrication, permits re-use of chip parts, and greatly increases the variety of materials that can be employed.

Figure 5A:
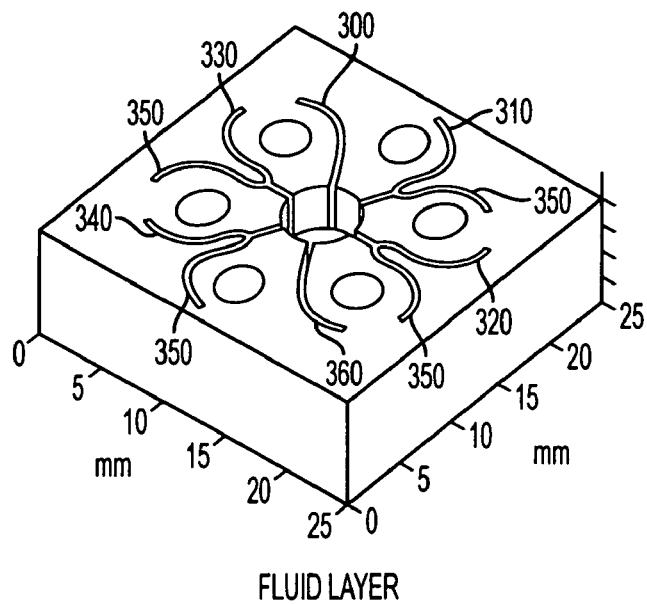
FIG. 5 is (a) fluid layer and (b) vent layer imaged by an FRT MicroProf® profilometer (vertical dimensions exaggerated) in one embodiment of the present application.
Figure 5B:
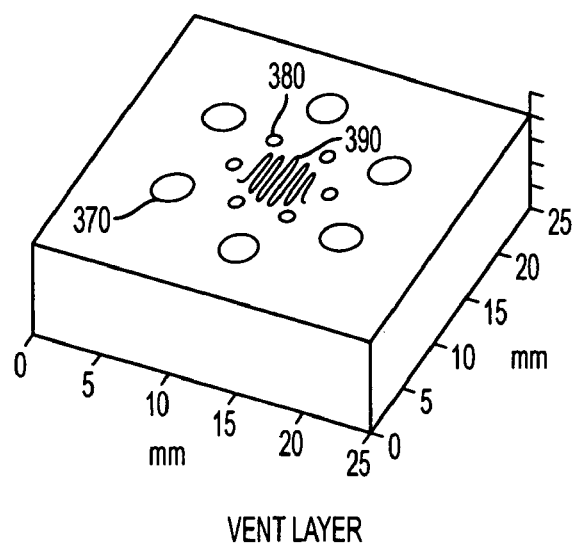

The fluid layer (FIG. 5a) of a representative synthesis chip contains a central cylindrical depression (5 mm diameter, 250 µm deep) that serves as the reaction chamber, and six grooves (250 µm wide, 250 µm deep) that serve as fluid inlet and outlet channels. The channels are curved around the holes used to bolt the chip together to maximize the gasket seal uniformity on top of the channels. These channels each contain ramped "walls" near the reactor, constituting the valve seats for the on-chip diaphragm valves (two are visible in FIG. 4). In addition, the fluidic layer contains a cylindrical counterbore directly beneath the reactor into which a heat-transfer rod is inserted to control the reactor temperature. Small ports are drilled from the outer end of each inlet/outlet channel through to the bottom surface of this layer, where individual O-rings will seal each port to the adapter interface in the instrument. The central reactor in the fluid layer of FIG. 5 is surrounded by six valve seats and microchannels, four of which have a T-junction (part of the priming mechanism). The vent layer contains a serpentine vacuum channel and holes to align the valve actuating rods on top of the valve seats.

In this embodiment, the gasket layer is a thin flat sheet of flexible material that serves three functions—it acts as a permeable gas-exchange membrane between the reactor in the fluid layer and the vacuum channel in the vent layer; it functions as the diaphragm in the on-chip microvalves, and it serves to seal the microchannels in the bottom and top layers (FIG. 5).

The vent layer (FIG. 5b) in this embodiment contains a rectangular groove (250 µm wide, 1 mm deep) following a serpentine path. In one particular arrangement, a vent configured above the reaction chamber is separated from the reaction chamber by a 100 µm gas permeable membrane. During solvent evaporations, vacuum is applied to this channel to facilitate the removal of solvent vapors transported across the gas-exchange membrane. Application of a vacuum to this vent allows fast removal of gas from the reaction chamber when the latter needs to be filled with fluid. As a result of this particular configuration, the evaporation process may be accelerated, and the process also reduces the vapor pressure, allowing removal of solvents at lower temperatures. Reduction of the vapor pressure reduces some of the stress on the closed on-chip valves during the evaporation steps. In certain configuration, the vent may be configured with two or more open ends in order to permit the flushing of the vapors that may condense inside and allows the removal of the vapors out of the chip, for example, by applying an inert gas such as nitrogen gas.

In this embodiment, integrated diaphragm microvalves are closed by metal rods (1 mm diameter), guided by holes in the vent layer, and driven by miniature pneumatic cylinders (FESTO EG2.5-10-PK-2). Six valves around the reactor control the flow of reagents and product, or can all be closed during heated reaction and evaporation steps.

The bypass portion of each inlet is connected to a check valve then to a single electronically-controlled dead-volume bypass valve.

In one embodiment, system components that can be under automatic control include an inert gas delivery source, a temperature control system, a pressure control system and one or more valves on the synthesis chip.

The temperature control system can operate somewhat autonomously. The desired temperature setpoint can be set by the computer software and can be changed during the synthesis run. The temperature control system automatically drives two relay output circuits to reach the target temperature: one for heating and one for cooling. The heater circuit can be an AC circuit (which can be switched on or off via computer) passing through a dimmer switch to control voltage and then to a heater cartridge that fits into the base of the microfluidic chip. The heater cartridge can be held in place by a small metal fixture. See FIGS. 8 and 9. This fixture can also contain a narrow hole into which a thermocouple is inserted to provide feedback of the current temperature at the base of the microfluidic chip back into the temperature control unit. The cooler circuit can be a DC circuit (which can be switched on or off via computer) that controls an electronic air valve. When open, this valve allows pressurized air to pass through a vortex cooler that blows cold air through several small channels in the metal fixture that holds the heater cartridge, and cools it down.

FIG. 9 discloses one possible attachment of the Vortex cooler via a Teflon elbow. The thermocouple is inserted into the adapter and sits very close to the top of the fixture "post" just below the microfluidic chip. The thermocouple feeds into the temperature control unit. The temperature control unit drives the circuit feeding the heating element (inserted beside the thermocouple up into the top "post"), and the circuit controlling the valve which turns the vortex cooler on and off.

To enable more rapid evaporation of solvents, the top part of the microfluidic chip can contain channels to which vacuum can be applied in order to provide a larger pressure differential between the microreactor below the solvent-exchange membrane and the space above. See e.g. "Microfluidic method and structure with an elastomeric gas-permeable gasket" U.S. Ser. No. 11/701,917, which is incorporated by reference herein in its entirety. Generally a vacuum pump is controlled via a digital signal under computer control (on/off). The vacuum pump can be connected through a charcoal and fiber vacuum trap (to collect fluids arising from leaks or condensing), through an electronically controlled 2-way valve, through the microfluidic chip, and through an electronic pressure gauge that can be read by the computer. The other side of the pressure gauge can be connected via a 2-way electronic valve to an inert gas pressure supply ($N_2$ or argon). This side is normally closed, but is present in one embodiment to allow the vacuum lines to be cleared out in case of leaks, and to allow the vent channels to be pressurized (if the vacuum valve is closed) to facilitate mixing in the microreactor, and to speed up filling of the reactor by pre-eliminating trapped air.

The hardware disclosed herein can be controlled for example by a PC-104 based system with 16 analog inputs, 10 analog outputs, 8 digital inputs, and 48 digital outputs. The controller can run embedded Windows-NT software that communicates via an Ethernet connection to a standard PC running the FIX32 automation software, an automation language that allows simple construction of graphical interfaces to visualize what is happening in the hardware and to control the various valves and other components. See FIG. 2, which is a display of the graphical control interface illustrating the fluid pathways (black lines) that connect system components. Electronic valves are represented by black circles with lines, and check valves are represented by diode symbols. The grey circle at the left is the rotary injector and the grey rectangle represents the microfluidic chip (six small circles are the on-chip valves). The interface allows manual operation by clicking on components to switch states, or automatic operation by selecting unit operations along the right side, each triggering a script to execute a sequence of steps.

In one embodiment, the control software can access individual digital outputs (2-way and 3-way valves, on-chip valves, temperature control system, heater enable, cooler enable, vacuum system, rotary injector) and analog outputs (temperature setpoint). Analog inputs (reactor temperature, vent channel pressure, radiation levels) are scaled to engineering units for monitoring on the main screen.

In addition to the interactive graphical interface in FIG. 2, dozens of scripts automate the process steps described herein. Each subprogram performs a sequence of simple operations such as changing the state of a valve, waiting for a fixed amount of time, or waiting for particular value of an input (e.g. heating until the reactor reaches a specified temperature).

One embodiment of the system has successfully been constructed, tested, and optimized. Currently it is capable of repeatably producing purified human-scale amounts of FDG in a semi-automated (each step in the radio-synthesis is initiated with a button on the computer screen) fashion.

In a fully-automated system the needed reaction times are optimized and a simple script in FIX32 is written to execute all the operations in sequence. A working example involves automated unit operations, such as filling, which in turn involve multiple sub-steps. The semi-automated "unit operation" scripts are designed to be "parameterized". That is, in a single place, an operator sets the flow times, reaction times, and heating temperatures, and the automated script reads all these and adjusts the synthesis run accordingly.

In one aspect, the present application discloses a fully automated hands free operation of the entire radio-synthesis cycle on a microfluidic device yielding purified PET radiotracer. In one embodiment, the instrument is portable, has no external components and is self-shielded, that is it does not require a separate hot cell. In yet another embodiment, the instrument comprises internal filters which enable operation without any additional exhaust, i.e. a true tabletop operation that doesn't require a fumehood.

In one embodiment the radiopharmaceutical produced is [F-18]FDG, the reagent is target water, and the radiotracer comprises F-18. In one embodiment, an instrument disclosed herein can rely on either ion-exchange or electrochemical F-18 trapping to isolate F-18 from target water.

In one aspect of the present application, pneumatically actuated reagents are metered by filling the reactor of fixed volume with liquid while displacing gas across a membrane (gasket) In this way, the amounts of reagents used in the reaction chamber are controlled by the microfluidic synthesis chip, which is self-metering. In contrast, flow through reactors either require a syringe pump or have the reagents flush right through in an uncontrollable manner since they have an outlet. In another aspect, the entire system is pressurized from a single compressed inert gas inlet, which can optionally be split into various pressures, as required inside the instrument. In one embodiment, the inert gas is nitrogen; in another embodiment the inert gas is argon. In yet another aspect, gas flow restrictors control the speed of reagent introduction into the chip and allow facilitation of mixing of reagents at high rates. In one embodiment, the pneumatic valve actuation system is placed above the synthesis chip as shown in FIG. 4. In one variation, the valve actuation system is compact enough to enable visualize the chip with a camera or a borescope. In another variation, formation of product in the reaction chamber is monitored with a borescope or a camera, held in place above the synthesis chip by the actuation plate.

In one embodiment, one or more reagents can be delivered from pre-filled individual vials or from a pre-packaged disposable cartridge. In one embodiment, the portable system can be cleaned without disassembly. Any of the reaction chamber, each of the reagent, product and waste channels can be cleaned, optionally in an automatic manner. The identity of the radiotracer produced can be easily changed without requiring hardware modifications. In one embodiment, the microfluidic synthesis chip can be exchanged. In one variation, the exchange of the synthesis chip can be performed by opening a single door in the lead shield, as opposed to disassembling the whole shield. In another embodiment, the final product vial is located in a separate shielded container so that the operator taking the product is not exposed to the rest of the radiation from the instrument.

In another embodiment, the instrument includes a heat-exchanger that allows rapid heating of the reaction chamber by a resistive heater and cooling of the reaction chamber by air in a vortex cooler.

According to one embodiment of the invention a computer system, or external input device, may be coupled to a program storage device and to a controller. The controller may be coupled to at least one valve on the synthesis chip, an inert gas delivery source, a temperature control system, a pressure monitor, and/or a vacuum system.

The general computer system includes a processing device, a system memory, a system bus coupling the system memory to the processing device, a storage device, such as a hard disk drive, a magnetic disk drive, e.g., to read from or write to a removable magnetic disk, and an optical disk drive, e.g., for reading a CD-ROM disk or to read from or write to other optical media. The storage device may be connected to the system bus by a storage device interface, such as a hard disk drive interface, a magnetic disk drive interface and an optical drive interface. Although this description of computer-readable media refers to a hard disk, a removable magnetic disk and a CD-ROM disk, it should be appreciated that other types of media that are readable by a computer system and that are suitable to the desired end purpose may be used, such as magnetic cassettes, flash memory cards, digital video disks, etc.

A user may enter commands and information into the general computer system or enter graphical information into the general computer system. A display device, such as a monitor, having a display screen, is connected to the system bus via an interface. In addition to the display screen, the general computer system can also include other peripheral output devices. The general computer system can operate in a networked environment using logical connections to one or more remote computer systems, such as a server, a router, a peer device or other common network node, and such a system can include any or all of the elements described relative to the general computer system.

When used in a local area network (LAN) environment, the general computer system is connected to the LAN through a network interface. When used in a WAN networking environment, the general computer system typically includes a modem or other means for establishing communications over a WAN, such as the Internet. The modem, which may be internal or external, may be connected to the system bus via the serial port interface. In a networked environment, program modules depicted relative to the general computer system, or portions thereof, may be stored in the remote memory storage device. It should be appreciated that the network connections shown are exemplary and other means of establishing a communications link between the computer systems may be used. It should also be appreciated that the application module could equivalently be implemented on host or server computer systems other than general computer systems, and could equivalently be transmitted to the host computer system by means other than a CD-ROM, for example, by way of the network connection interface. Program modules stored in the drivers of the computer system may control how the general computer system functions and interacts with the user, with I/O devices or with other computers. Program modules may include routines, operating systems, target application program modules, data structures, browsers, and other components.

It should be appreciated that no particular programming language is described for carrying out the various procedures described in the detailed description because it is considered that the operations, steps, and procedures described herein are sufficiently disclosed to permit one of ordinary skill in the art to practice an exemplary embodiment of the present application. Moreover, there are many computers and operating systems which may be used in practicing an exemplary embodiment, and therefore no detailed computer program could be provided which would be applicable to all of these many different systems. Each user of a particular computer should be aware of the language and tools which are most useful for that user's needs and purposes.

Moreover, the method may be embodied in the form of computer-implemented processes and apparatuses for practicing those processes. The above may also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. Existing systems having reprogrammable storage (e.g., flash memory) can be updated to implement the invention. The above can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments may configure the microprocessor to create specific logic circuits in whole or in part.

EXAMPLES

Both the fluid and vent layers and adapter interface were fabricated from pDCPD, a rigid, transparent polymer developed by Materia Incorporated. This polymer has good machining properties, allowing rapid prototyping of intricate chip designs by CNC, including minute chamfers to remove sharp burrs from channels and valve seats.

The gasket layer must be both strong (for reliable valve operation) and gas-permeable (for rapid evaporation of $H_2O$ and $CH_3CN$). Numerous materials were evaluated and good results were obtained with a layered composite of 25-30 μm of polydimethylsiloxane (PDMS, Dow-Corning Sylgard® 184) on top of 15-20 μm of an optimized perfluoropolyether (Liquidia Technologies FluoroCur™), each cured separately after spin-coating. The PDMS is very permeable and provides strength; the FluoroCur™ is less permeable but protects PDMS against attack by F-18.

Extensive experiments confirmed resistance to solvents, stability above 140° C. (peak temperature of reactions and evaporations), and compatibility with reactions. Less than 3% adsorption of F-18 (ion, intermediates, or product) onto pDCPD and less than 1% onto FluoroCur™ was measured.

Figure 6:
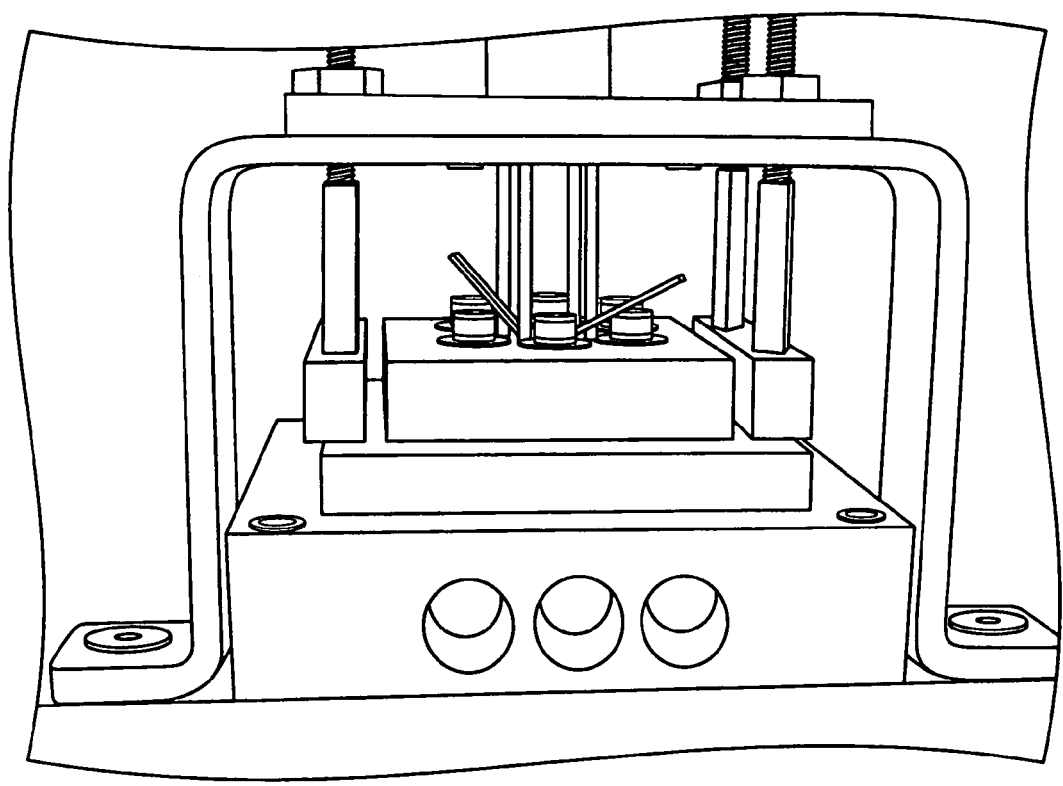
FIG. 6 is a photograph of a microfluidic chip clamped to an adapter manifold to form a tight seal at the O-ring interface.

To connect to the external (macroscopic) fluid handling system, the chip is installed on a plastic fluidic adapter manifold (FIG. 6). Tubing connects to the adapter via threaded fittings and the chip seals to a flat surface of the adapter via a set of perfluoroelastomer O-rings.

The gap between macrofluidic and microfluidic volumes is bridged by a novel mechanism utilizing the on-chip valves and portions of the microfluidic inlet channels to allow rapid automatic priming of reagent lines up to the reactor (FIG. 7). When the on-chip valve is closed, the reagent flows into the chip, through the "loop" and out to waste, allowing rapid elimination of any trapped air in the line. Once the line is primed, the reagent can be instantly delivered into the reactor by opening the on-chip valve and simultaneously closing a valve in the external waste line to provide a back-pressure. The connections to the chip and external fluidic system can be seen clearly in the lower figure. Priming saves valuable time by eliminating the need to push large volumes of air trapped in the tubing through the gas-exchange membrane as each reagent is added by dead-end filling.

Temperature Control: An insulated metal heat transfer rod is inserted into the bottom of the microfluidic chip, the tip of the rod sitting only about 0.5 mm below the reactor, to provide localized heating (FIGS. 8 and 9). The top portion of the rod contains a 50W Watlow FireRod® cartridge heater and a thermocouple, and the base of the rod contains a network of channels through which cold air can be supplied by the attached Exair vortex tube. Active heating and cooling elements are controlled by an Ogden ETR3400-4111115 temperature controller. This system can switch the rod temperature between room temperature and 140° C. in about 45 sec in either the heating or cooling direction. Experiments in which a thermocouple was placed inside the microreactor allowed us to calibrate the temperature lag between the tip of the heat transfer rod and the reactor.

Vacuum system: The two ends of the channel in the upper layer of the microfluidic chip are connected to a single-stage vacuum pump (KNF MPU953) and a pressure supply, each controlled by a 2-way valve. A charcoal trap in the vacuum line collects liquid and can be mounted in a dose calibrator to monitor F-18 losses due to formation of volatile compounds during synthesis. An approximate reading of the pressure inside the vent channel is provided by an electronic gauge, allowing occlusions to be detected and evaporation progress to be monitored.

Fluid System The complete fluidic system is shown in FIG. 10. Reagents are pre-loaded into vials containing a fluid delivery line extending to the bottom of the vial and a pressure delivery line in the headspace of the vial. Reagents are pushed through the system by pressurized nitrogen (typically 15-30 psi) under the control of reagent pressure valves. Between each reagent vial and the chip adapter interface, the reagent line joins a selection valve that determines whether the reagent or a wash solvent is delivered to the chip. Reagents that use a priming loop have an associated waste line running out from the adapter interface to a common waste manifold and 2-way valve.

Radiation shielding Integrated shielding is one feature that makes the instruments disclosed herein independent from traditional hot cells and radiopharmacies. In one embodiment, shielding consisted of a box built from 18 interlocking 0.565"-thick lead panels (2000 lb total). In another embodiment, the production instrument can have lead components minimized, shielding only critical components and detectors, thus yielding a lighter and more portable instrument.

For the particular example of $^{18}$F-FDG synthesis, the reagents include: (i) MT, mannose triflate in acetonitrile (precursor), (ii) HCl, hydrochloric acid (hydrolysis agent used in deprotection reaction), (iii) $K_2CO_3$ solution (elutes F-18 from ion exchange column), (iv) K222, Kryptofix2.2.2 in acetonitrile (to solvate the F-18 in preparation for fluorination reaction), (v) water (used for elution of FDG out of the microfluidic synthesis chip, and dilution of product), (vi) [F-18] fluoride ion in [O-18]$H_2O$ (radioactive label).

Synthesis of FDG was carried out according to the following process steps. The many parameters for each step (temperatures, heating times, flow times, etc.) can easily be adjusted to optimize the process.

1) F-18 concentration. Dilute F-18 is delivered from the cyclotron in 1.8 mL of [O-18]$H_2O$ to the F-18 vial, then is flowed through an AG 1-X8 resin exchange column to trap F-18. Concentration by a factor of about 350× is achieved by eluting with 5 μL of 0.5M $K_2CO_3$ directly into the microreactor through the F-18 inlet. By eluting with several plugs of 1-2 μL volume separated by nitrogen, 79% of F-18 could be transferred. To achieve a low-volume fluid pathway between the $K_2CO_3$ vial and the chip, small diameter tubing and a rotary injection valve with minimized internal volume (Rheodyne 9910-000) were used.

2) Phase transfer. Water is evaporated by closing all on-chip valves and heating the reactor to 105° C. with the vacuum on. Next, the reactor is filled with Kryptofix 222 (K222, 50 mg/mL in $CH_3CN$) to solvate F-18 in the organic phase. Next, the reactor is closed and heated to about 105° C. to evaporate solvent. Note that all filling steps involve priming of the reagent line and opening of the on-chip valve while the reagent vial is pressurized. Typically, >10% of the reactor is left empty because the remaining gas bubble is a convenient monitor of evaporation progress.

3) Fluorination reaction. The precursor mannose triflate (25 mg/mL in $CH_3CN$) is then introduced into the reactor where it mixes with F-18/K222 and is reacted at 105° C. to form the intermediate fluoro-1,3,4,6-tetra-O-acetyl-D-glucose (FTAG). Heating continues until about 65% of the solvent has evaporated.

4) Deprotection reaction. 1 M HCl is then added to the reactor to deprotect the FTAG and yield FDG. After filling the reactor, the contents are heated to 105° C. for 10 min. As in other steps, HCl is introduced while there is still $CH_3CN$ from the previous step left in the reactor in order to facilitate improved dissolution and mixing.

5) Elute product from reactor. The FDG inside the reactor is eluted with 10-15 mL water into a collection vial, optionally passing through a purification column.

After synthesis, all lines can be washed and dried to avoid cross-contamination on subsequent runs or to avoid dripping on the O-ring interface when chips are exchanged.

Using similar microfluidic technology we have also demonstrated the synthesis of 2-(1,1-dicyanopropen-2-yl)-6-(2-[18F]fluoroethyl)-methylamino)-naphthalene ([F-18]FDDNP) and 3'-[18F]fluoro-3'-deoxy-L-thymidine ([F-18]FLT).

Figure 2A:
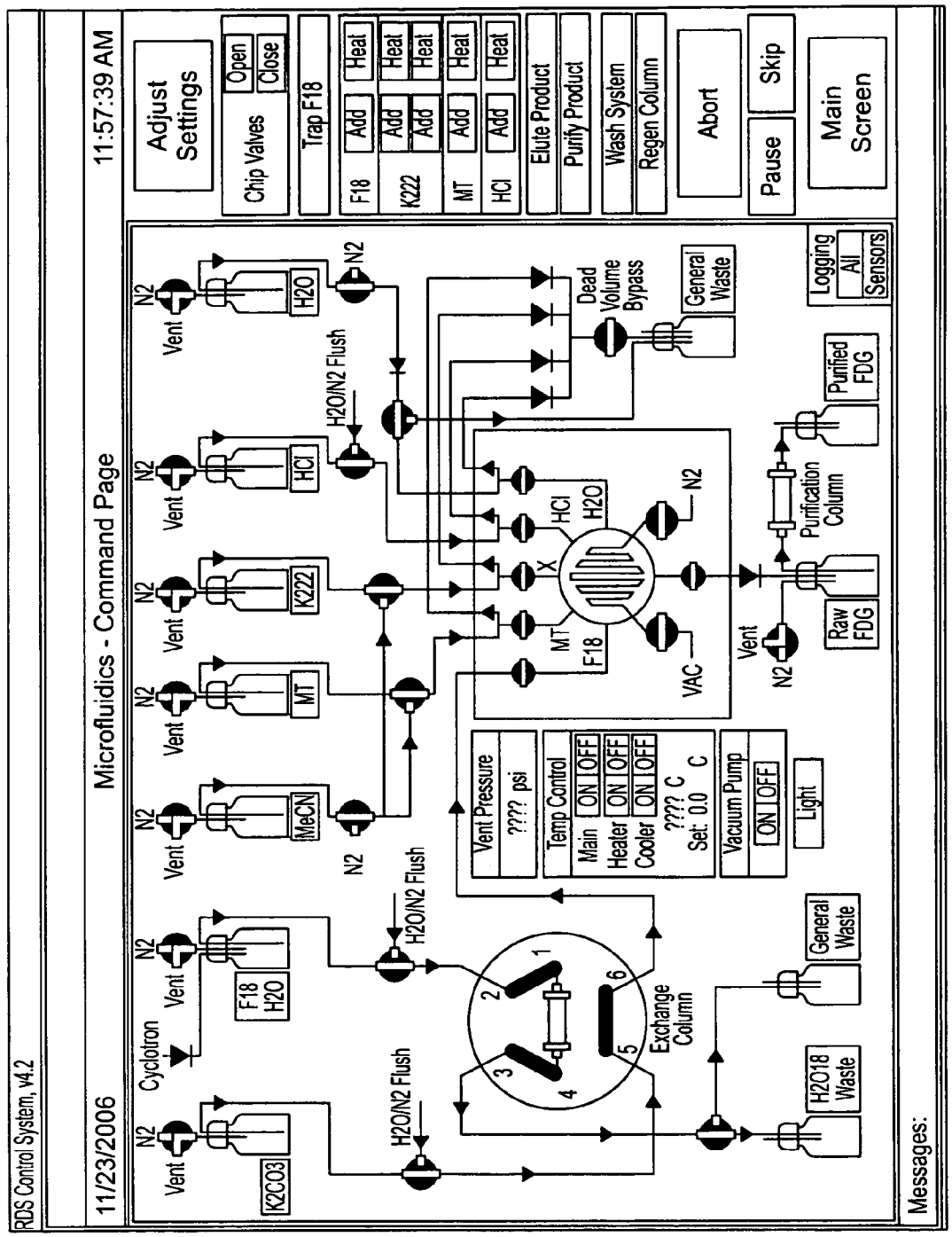
Figure 2B:
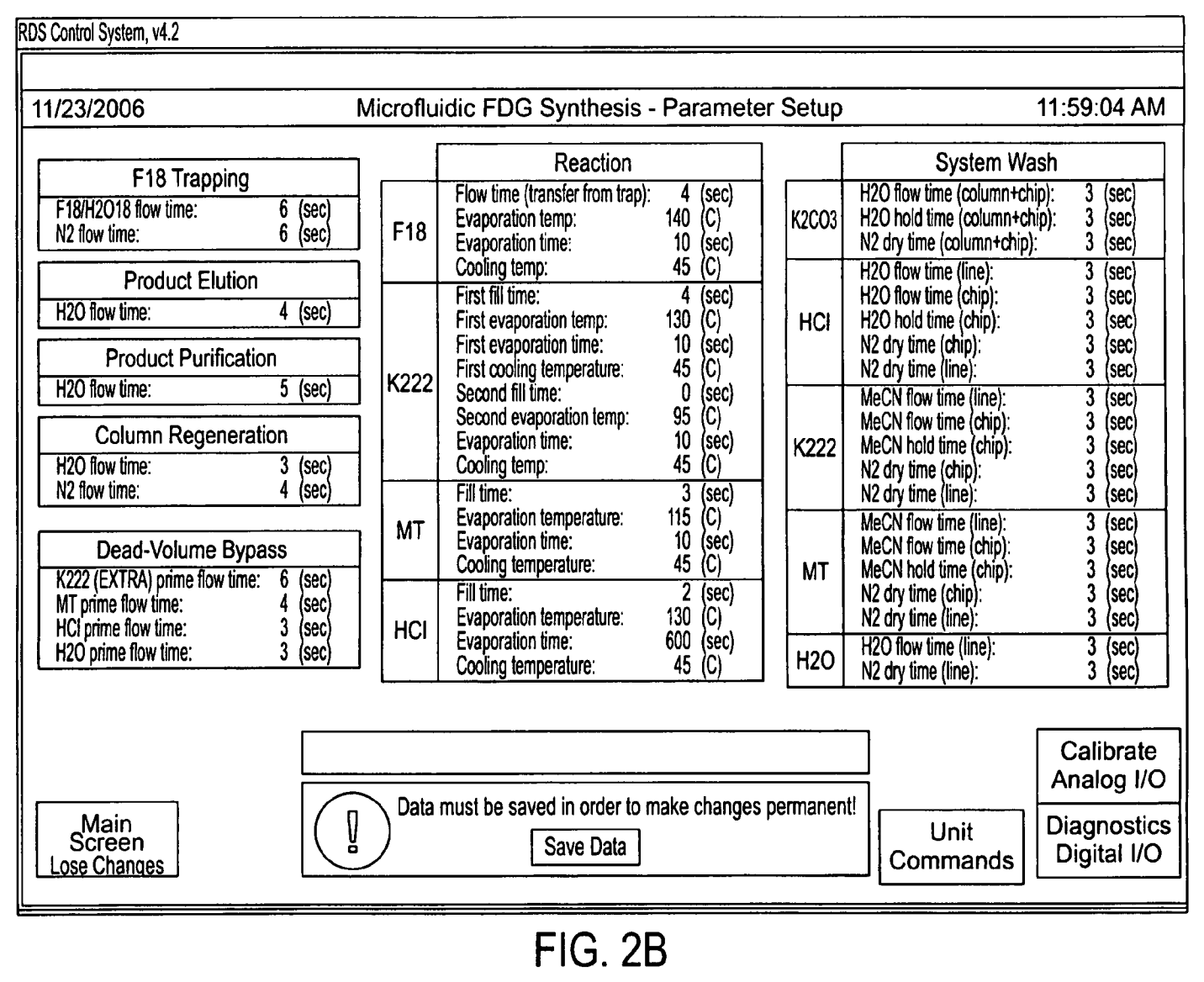

As exemplified in FIG. 2b, a number of variables can be defined by the operator before operation of the automated system disclosed herein, such as is represented by FIG. 2a or FIG. 1.

For a process utilizing a carbon-11-labeling agent (e.g., methyl iodide, methyl triflate, carbon monoxide, hydrogen cyanide), any of the following steps can be performed within a microfluidic device:

a) Receive [$^{11}$C]-labeling agent from the cyclotron target or post-irradiation processor b) Generate a solution of reactive [$^{11}$C]-labeling agent in an organic and/or polar aprotic solvent (acetonitrile, DMF, DMSO, etc.)

c) Provide a solution of a reactive precursor in an organic and/or polar aprotic solvent (acetonitrile, DMF, DMSO, etc.)

d) React the [$^{11}$C]-labeling agent with the precursor using a $S_N2$ nucleophilic substitution reaction or other suitable reaction to create a new carbon-nitrogen, carbon-oxygen, carbon-sulfur or carbon-carbon bond, using heat or microwave energy if necessary e) Purify the initial [$^{11}$C]-labeled product by, for example, solid phase extraction or chromatography f) React the purified initial [$^{11}$C]-labeled product with a second reagent to generate the final [$^{11}$C]-labeled product (e.g., hydrolysis of protecting group(s), if necessary)

g) Purify the final [$^{11}$C]-labeled product by solid phase extraction or chromatography h) Remove solvents from the [$^{11}$C]-labeled product i) Deliver the final [$^{11}$C]-labeled product to a final product vial.

All references cited herein are incorporated by reference as if each had been individually incorporated by reference in its entirety. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

What is claimed:

1. A microfluidic system for synthesis of a radiolabeled compound, the system configured to transfer and facilitate the reaction of microliters and/or nanoliters of reagent, the system comprising:
   a microfluidic synthesis chip configured for conducting batch reactions, the chip comprising;
   a reaction chamber;
   an inlet flow channel in communication with the reaction chamber and configured to pass reagent into the reaction chamber, the inlet flow channel having a valve configured to regulate flow to the reaction chamber; and
   a plurality of outlet channels in communication with the reaction chamber and configured to pass reagent out of the reaction chamber, each channel having a valve configured to close to trap reagent within the reaction chamber during a reaction and release reagent and products when the reaction is complete; and
   a reagent source comprising at least one reagent, the reagent source in fluid communication with the reaction chamber via the at least one flow channel,
   wherein the reaction chamber has an area substantially greater than a cross-sectional area of each of the inlet flow channel and the outlet channels.

2. The system of claim 1, further comprising a purification system in fluid communication with the synthesis chip, a product receptacle in fluid communication with said purification system, and radiation shielding substantially enclosing one or more of:
   a) the reagent source
   b) microfluidic chip;
   c) the purification system; and
   d) the product receptacle.

3. The system of claim 1, wherein said system does not require a separate hot cell.

4. The system of claim 1, further comprising a temperature control system operatively coupled to the microfluidic chip, the temperature control system comprising a heat-exchanger.

5. The system of claim 1, wherein said inlet flow channel valves and outlet flow channel valves are selected from the group consisting of a check valve and a 3-way valve.

6. The system of claim 1, further comprising a gas source in communication with the reagent source such that, the system is pressurized by gas from said inlet and the speed with which said reagents are conveyed from said source to said reaction chamber is controlled by pressure of gas.

7. The system of claim 6, further comprising a gas permeable membrane adjacent the reaction chamber and wherein the speed with which said reagents are conveyed from said reagent source to said reaction chamber is controlled by the thickness and/or composition of said membrane.

8. The system of claim 2, further comprising a vacuum in communication with the reaction chamber, wherein the radiation shield substantially encloses the vacuum.

9. A portable microfluidic system for synthesis of a radiolabeled compound, the system configured to transfer and facilitate the reaction of microliters and/or nanoliters of reagent, the system comprising:
   a microfluidic synthesis chip configured to conduct batch reactions comprising:
   a reaction chamber;
   a vent in communication with the reaction chamber;
   at least one flow channel in communication with the reaction chamber;
   at least one valve configured to regulate flow to or from the reaction chamber; and
   a reagent source comprising at least one reagent in fluid communication with the reaction chamber via the flow channel; and
   a filter in communication with the reaction chamber and an area outside of the system, the filter configured to filter exhaust from the reaction chamber wherein the valve is configured to close to trap reagent within the reaction chamber during a reaction during a reaction and release reagent and products when the reaction is complete.

10. The system of claim 1, wherein the inlet and outlet channels have a cross-section of no more than about 300 μm.

11. The system of claim 1, wherein the reagent source contains about 5 μL to about 50 μL of reagent.

12. The system of claim 1, wherein the reaction chamber has a diameter and a height, wherein the diameter is about 1,000 μm to about 20,000 μm and the diameter to height ratio is about 3 to about 10.

13. The system of claim 9, further comprising a gas source in communication with the at least one reagent such that gas conveys the at least one reagent to the reaction chamber.

14. The system of claim 13, wherein the microfluidic chip further comprises a gas permeable membrane in communication with the reaction chamber.

15. The system of claim 14, wherein the vent is in communication with the gas permeable membrane.

16. The system of claim 9, further comprising a vacuum in communication with the reaction chamber and the filter.

17. The system of claim 9, further comprising a radiation shield substantially enclosing the microfluidic chip and the filter.

18. The system of claim 16, further comprising a radiation shield substantially enclosing the microfluidic chip, the filter and the vacuum.

19. The system of claim 9, wherein the flow channel has a cross-section of no more than about 300 μm.

20. The system of claim 19, wherein the reagent source contains about 5 μL to about 1000 μL of reagent.

21. The system of claim 19, wherein the reagent source contains about 5 μL to about 15 μL of reagent.

22. The system of claim 19, wherein the reaction chamber has a diameter and a height, wherein the diameter is about 1,000 μm to about 20,000 μm and the diameter to height ratio is about 3 to about 10.

23. The system of claim 15, wherein the gas-permeable membrane is positioned between the reaction chamber and the vent.

24. The system of claim 23, wherein the vent is about 250 μm wide and about 1000 mm deep.

25. The system of claim 18, wherein filter is in communication with an area outside of the radiation shield via the vacuum.

26. The system of claim 9, further comprising a trap chip or cartridge upstream of and in communication with the microfluidic chip.

27. The system of claim 26, wherein the reagent source comprises a plurality of reagent sources, one reagent source comprising $^{18}F$—$H_2O$ and one reagent source comprising $K_2CO_3$ upstream of the trap chip or cartridge.

28. The system of claim 13, further comprising:
a temperature control system operatively coupled to the microfluidic chip, the temperature control system comprising a heat exchanger;
a pressure control system operatively coupled to the microfluidic chip, the pressure control system comprising a vacuum;
a controller operatively coupled to and controlling the function of at least one component selected from the group consisting of the gas delivery source, the vacuum system, the temperature control system and the valve on the synthesis chip; and
at least one external input device coupled to the controller.

29. The system of claim 27, wherein one reagent source comprises MeCN, one reagent source comprises mannose triflate, one reagent source comprises K222, one reagent source comprises HCl and one reagent source comprises $H_2O$, wherein each reagent source is upstream of the microfluidic chip.

30. The system of claim 9, further comprising at least one controller operatively coupled to and controlling the function of at least one component selected from the group consisting of the gas delivery source, the reagent source and the microfluidic chip valve.

31. A microfluidic system for synthesis of a radiolabeled compound, the system configured to transfer and facilitate the reaction of microliters and/or nanoliters of reagent, the system comprising:
a microfluidic synthesis chip configured to conduct batch reactions, the microfluidic synthesis chip comprising:
a substrate comprising:
a reaction chamber;
an inlet channel in communication with the reaction chamber and configured to pass reagent into the reaction chamber, the inlet channel comprising a valve configured to regulate flow to the reaction chamber;
an outlet channel in communication with the reaction chamber and configured to pass reagent out of the reaction chamber, the outlet channel having a valve configured to control reagent and product flow out of the reaction chamber;
a gas permeable membrane in communication with the reaction chamber;
a vent in communication with the reaction chamber;
a reagent source in fluid communication with the reaction chamber via the inlet channel; and
a gas source in communication with the at least one reagent such that gas conveys the reagent to the reaction chamber,
wherein the valve of the outlet channel is configured to close to trap reagent within the reaction chamber during a reaction and release reagent and products when the reaction is complete.

32. The system of claim 31, wherein the reaction chamber has a diameter and a depth, the diameter substantially larger than the depth.

33. The system of claim 31, wherein the gas permeable membrane is positioned between the reaction chamber and the vent and wherein the gas permeable membrane is in communication with the vent.

34. The system of claim 31, wherein the channel has a cross-section no greater than about 300 μm.

35. The system of claim 31, wherein the reagent source contains no more than about 1000 μL of reagent.

36. The system of claim 32, wherein the diameter of the reaction chamber is about 1,000 μm to about 20,000 μm and the diameter to height ratio is about 3 to about 10.

37. The system of claim 36, wherein the height of the reaction chamber is about 250 μm.

38. The system of claim 31, wherein the gas-permeable membrane defines a portion of the reaction chamber.

39. The system of claim 31, wherein the microfluidic chip further comprises a plurality of outlet channels in communication with the reaction chamber, each channel configured to pass reagents and products out of the reaction chamber, each channel having a valve configured to trap reagent within the reaction chamber during a reaction and release reagent and products when the reaction is complete.

40. The system of claim 26, wherein the trap chip or cartridge comprises an ion-exchange column having a resin of about 1 μL to about 3 μL.

41. The system of claim 26, wherein the trap chip or cartridge comprises an ion-exchange column having a resin with about 8% cross-linking.

42. The system of claim 41, wherein the resin has a dry mesh size of about 50 to about 400.

43. The system of claim 9, wherein the reagent source comprises microliters or nanoliters of liquid.

44. The system of claim 9, wherein the reaction chamber has a rounded wall.

45. The system of claim 31, wherein the reaction chamber has a rounded wall.

* * * * *